US007291492B2

(12) United States Patent
Zelent et al.

(10) Patent No.: US 7,291,492 B2
(45) Date of Patent: Nov. 6, 2007

(54) HISTONE DEACETYLASE 9

(75) Inventors: Arthur Zelent, London (GB); Kevin Petrie, Madrid (ES); Fabien Guidez, London (GB)

(73) Assignee: The Institute of Cancer Research, London (GB)

( * ) Notice: Subject to any disclaimer, the term of this patent is extended or adjusted under 35 U.S.C. 154(b) by 0 days.

(21) Appl. No.: 10/491,372

(22) PCT Filed: Oct. 2, 2002

(86) PCT No.: PCT/GB02/04455

§ 371 (c)(1),
(2), (4) Date: Sep. 2, 2004

(87) PCT Pub. No.: WO03/029451

PCT Pub. Date: Apr. 10, 2003

(65) Prior Publication Data

US 2005/0130146 A1 Jun. 16, 2005

(30) Foreign Application Priority Data

Oct. 2, 2001 (GB) ................................ 0123664.5

(51) Int. Cl.
*C12N 9/16* (2006.01)
*C12P 1/00* (2006.01)
*C12P 21/04* (2006.01)

(52) U.S. Cl. ........................ 435/196; 435/41; 435/71.1

(58) Field of Classification Search ..................... None
See application file for complete search history.

(56) References Cited

FOREIGN PATENT DOCUMENTS

| | | |
|---|---|---|
| WO | WO 01/42437 | 6/2001 |
| WO | WO 02/36783 | 5/2002 |
| WO | WO 02/50285 | 6/2002 |
| WO | WO 02/102323 A2 | 12/2002 |
| WO | WO 02/102984 | 12/2002 |

OTHER PUBLICATIONS

Manlknecht et al., Chromosomal organization and localization of the human histone deacetylase 9 gene (HDAC9). Biochem Biophys Res Commun. Apr. 26, 2002;293(1):182-91.*

Protein Sequence Searches—Feb. 2005 "us-10-491-372-1.rup" pp. 1-7.*

Zhow et al., Cloning and characterization of a histone deacetylase, HDAC9. PNAS Sep. 11, 2001 vol. 98 No. 19 10572-10577.*

Nagase et al., Prediction of the coding sequences of unidentified human genes. XI. The complete sequences of 100 new cDNA clones from brain which code for large proteins in vitro.*

Wang et al., HDAC4, a human histone deacetylase related to yeast HDA1, is a transcriptional corepressor.Mol Cell Biol. Nov. 1999;19(11):7816-27.*

Zhou, X., et al., "Cloning and characterization of a histone deacetylase, HDAC9", pp. 10572-10577, P.N.A.S., vol. 98, Sep. 2001; and associated NCBI Accession No. AY032737.

N. R. Bertos, et al., "Class II histone deacetylases: Structure, function and regulation", Biochem. Cell Biol., vol. 79: pp. 243-252, 2001.

Petrie, F.G., et al., "Role of a novel Class II histone deacetylase in normal and leukemia-associated transcriptional repression", Blood, vol. 98, p. 568a, 2001, (abstract).

Wang, A.H., et al., "HDAC4, a Human Histone Deacetylase Related to Yeast HDA1, Is a Transcriptional Corepressor", Molecular and Cellular Biology, vol. 19, pp. 7816-7827, Nov. 1999.

Kao, H.-Y., et al., "Isolation of a novel histone deacetylase reveals that class I and class II deacetylases promote SMRT-mediated repression", Genes & Development, vol. 14, pp. 55-66, Jan. 2000.

Yoshida, M., et al., "Potent and Specific Inhibition of Mammalian Histone Deacetylase Both in Vivo and in Vitro by Trichostatin A*", J. of Biol. Chem., vol. 265, pp. 17174-17179, Oct. 1990.

Nagase, T., et al.,."Prediction of the Coding Sequences of Unidentified Human Genes. XI. The Complete Sequences of 100 New cDNA Clones from Brain Which Code for Large Proteins in vitro", DNA Research, vol. 5, pp. 277-286, 1998.

U.S. Appl. No. 60/298,296, filed Jun. 14, 2001, Bristol-Myers Squibb Company.

Grozinger, Christina M. et al., *Three proteins define a class of human histone deacetylases related to yeast Hda1p*. Proc. Natl. Acad. Sci. USA, 96: 4868-73 (1990).

Petrie, Kevin et al., *The Histone Deacetylase 9 Gene Encodes Multiple Protein Isoforms*, The Journal of Biological Chemistry, 278(18): 16059-16072 (2003).

* cited by examiner

*Primary Examiner*—Joseph Woitach
*Assistant Examiner*—Maria Leavitt
(74) *Attorney, Agent, or Firm*—Dann, Dorfman, Herrell, & Skillman, P.C.; Kathleen D. Rigaut; Robert C. Netter

(57) ABSTRACT

The identification and cloning of histone deacetylase 9 (HDAC9) is disclosed, and in particular full length HCAC9 polypeptides and HDAC9 polypeptides which have deacetylase activity, and to nucleic acid molecules encoding these polypeptides. The uses of these polypeptides and nucleic acid molecules are disclosed, for example for screening for compounds that are capable of modulating HDAC9 biological activity.

7 Claims, 17 Drawing Sheets

(Part 1 of 2)

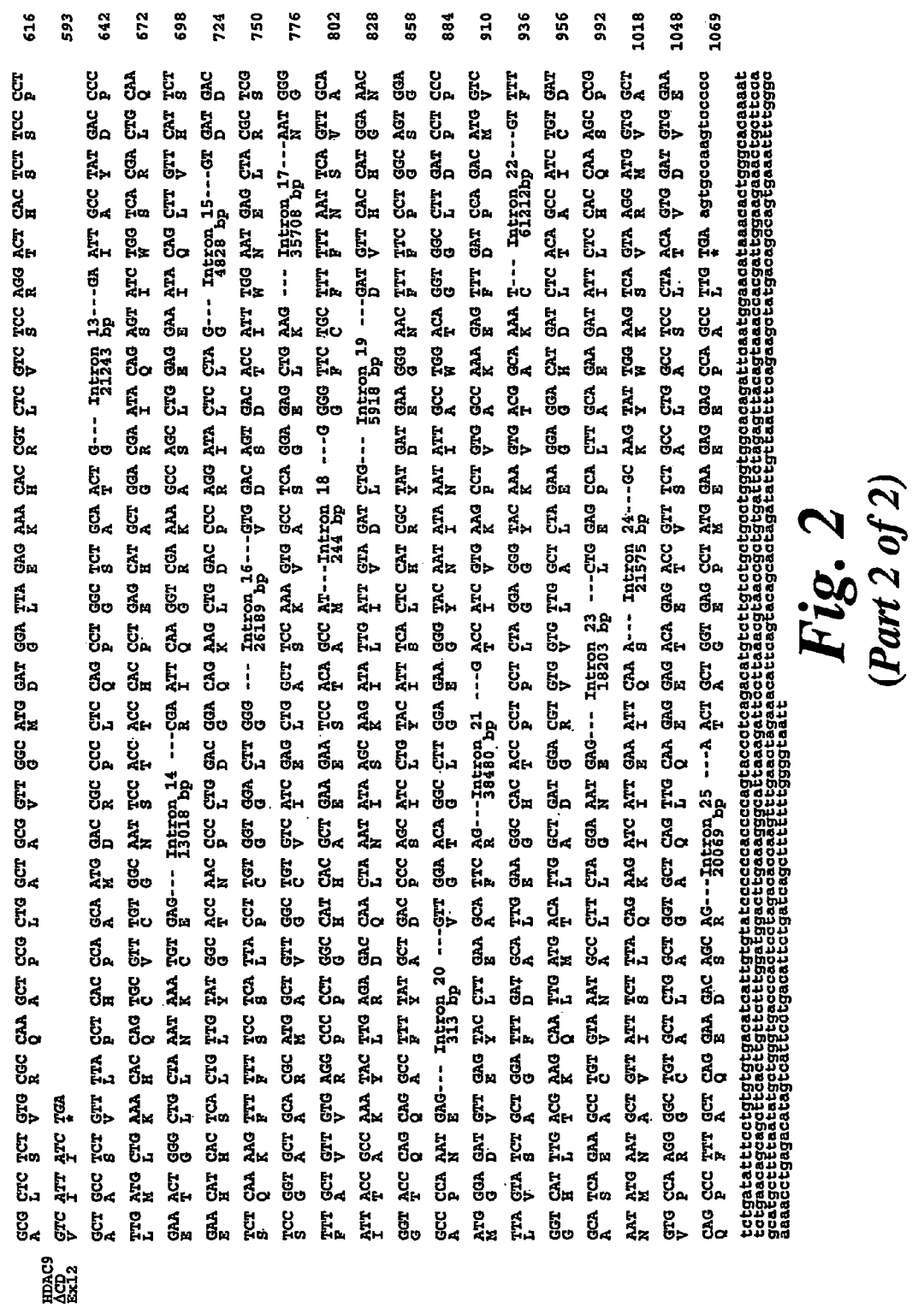

```
      GCG CTC TCT GTG CGC CAA GCT CCG CTG GCT GCG GTT GGC ATG GAT GGA TTA GAG AAA CAC CGT CTC GTC TCC AGG ACT CAC TCT TCC CCT
      A   L   S   V   R   Q   A   P   L   A   A   V   G   M   D   G   L   E   K   H   R   L   V   S   R   T   H   S   S   P    616
HDAC9
ΔCD   GTC ATT ATC TGA
Ex12  V   I   I   *                                                                                                          593

GCT GCC TCT GTT TTA CCT CAC CCA GCA ATG GAC CGC CCC CTC CAG CCT GGC TCT GCA ACT G--- Intron 13---GA ATT GCC TAT GAC CCC
A   A   S   V   L   P   H   P   A   M   D   R   P   L   Q   P   G   S   A   T   G       21243 bp       I   A   Y   D   P    642

TTG ATG CTG AAA CAC CAG TGC GTT TGT GGC AAT TCC ACC ACC CAC CCT GAG CAT GCT GGA CGA ATA CAG AGT ATC TGG TCA CGA CTG CAA
L   M   L   K   H   Q   C   V   C   G   N   S   T   T   H   P   E   H   A   G   R   I   Q   S   I   W   S   R   L   Q    672

GAA ACT GGG CTG CTA AAT AAA TGT GAG--- Intron 14 ---CGA ATT CAA GGT CGA AAA GCC AGC CTG GAG GAA ATA CAG CTT GTT CAT TCT
E   T   G   L   L   N   K   C   E      13018 bp     R   I   Q   G   R   K   A   S   L   E   E   I   Q   L   V   H   S    698

GAA CAT CAC TCA CTG TTG TAT GGC ACC AAC CCC CTG GAC GGA CAG AAG CTG GAC CCC AGG ATA CTC CTA G--- Intron 15---GT GAT GAC
E   H   H   S   L   L   Y   G   T   N   P   L   D   G   Q   K   L   D   P   R   I   L   L   G       4828 bp       D   D    724

TCT CAA AAG TTT TTT TCC TCA TTA CCT TGT GGT GGA CTT GGG --- Intron 16---GTG GAC AGT GAC ACC ATT TGG AAT GAG CTA CGC TCG
S   Q   K   F   F   S   S   L   P   C   G   G   L   G       26189 bp     V   D   S   D   T   I   W   N   E   L   R   S    750

TCC GGT GCT GCA CGC ATG GCT GTT GGC TGT GTC ATC GAG CTG GCT TCC AAA GTG GCC TCA GGA GAG CTG AAG --- Intron 17---AAT GGG
S   G   A   A   R   M   A   V   G   C   V   I   E   L   A   S   K   V   A   S   G   E   L   K       35708 bp     N   G    776

TTT GCT GTT GTG AGG CCC CCT GGC CAT CAC GCT GAA GAA TCC ACA GCC AT---Intron 18 ---G GGG TTC TGC TTT TTT AAT TCA GTT GCA
F   A   V   V   R   P   P   G   H   H   A   E   E   S   T   A   M     244 bp         G   F   C   F   F   N   S   V   A    802

ATT ACC GCC AAA TAC TTG AGA GAC CAA CTA AAT ATA AGC AAG ATA TTG ATT GTA GAT CTG--- Intron 19 ---GAT GTT CAC CAT GGA AAC
I   T   A   K   Y   L   R   D   Q   L   N   I   S   K   I   L   I   V   D   L      5918 bp      D   V   H   H   G   N    828

GGT ACC CAG CAG GCC TTT TAT GCT GAC CCC AGC ATC CTG TAC ATT TCA CTC CAT CGC TAT GAT GAA GGG AAC TTT TTC CCT GGC AGT GGA
G   T   Q   Q   A   F   Y   A   D   P   S   I   L   Y   I   S   L   H   R   Y   D   E   G   N   F   F   P   G   S   G    858

GCC CCA AAT GAG--- Intron 20 ---GTT GGA ACA GGC CTT GGA GAA GGG TAC AAT ATA AAT ATT GCC TGG ACA GGT GGC CTT GAT CCT CCC
A   P   N   E         313 bp     V   G   T   G   L   G   E   G   Y   N   I   N   I   A   W   T   G   G   L   D   P   P    884

ATG GGA GAT GTT GAG TAC CTT GAA GCA TTC AG---Intron 21 ---G ACC ATC GTG AAG CCT GTG GCC AAA GAG TTT GAT CCA GAC ATG GTC
M   G   D   V   E   Y   L   E   A   F   R     38480 bp      T   I   V   K   P   V   A   K   E   F   D   P   D   M   V    910

TTA GTA TCT GCT GGA TTT GAT GCA TTG GAA GGC CAC ACC CCT CCT CTA GGA GGG TAC AAA GTG ACG GCA AAA T--- Intron 22---GT TTT
L   V   S   A   G   F   D   A   L   E   G   H   T   P   P   L   G   G   Y   K   V   T   A   K   C       61212bp        F    936

GGT CAT TTG ACG AAG CAA TTG ATG ACA TTG GCT GAT GGA CGT GTG GTG TTG GCT CTA GAA GGA GGA CAT GAT CTC ACA GCC ATC TGT GAT
G   H   L   T   K   Q   L   M   T   L   A   D   G   R   V   V   L   A   L   E   G   G   H   D   L   T   A   I   C   D    956

GCA TCA GAA GCC TGT GTA AAT GCC CTT CTA GGA AAT GAG--- Intron 23 ---CTG GAG CCA CTT GCA GAA GAT ATT CTC CAC CAA AGC CCG
A   S   E   A   C   V   N   A   L   L   G   N   E      18203 bp      L   E   P   L   A   E   D   I   L   H   Q   S   P    992

AAT ATG AAT GCT GTT ATT TCT TTA CAG AAG ATC ATT GAA ATT CAA A--- Intron 24---GC AAG TAT TGG AAG TCA GTA AGG ATG GTG GCT
N   M   N   A   V   I   S   L   Q   K   I   I   E   I   Q   S       21575 bp    K   Y   W   K   S   V   R   M   V   A   1018

GTG CCA AGG GGC TGT GCT CTG GCT GGT GCT CAG TTG CAA GAG GAG ACA GAG ACC GTT TCT GCC CTG GCC TCC CTA ACA GTG GAT GTG GAA
V   P   R   G   C   A   L   A   G   A   Q   L   Q   E   E   T   E   T   V   S   A   L   A   S   L   T   V   D   V   E   1048

CAG CCC TTT GCT CAG GAA GAC AGC AG---Intron 25 ---A ACT GCT GGT GAG CCT ATG GAA GAG GAG CCA GCC TTG TGA agtgccaagtccccc
Q   P   F   A   Q   E   D   S   R     20069 bp      T   A   G   E   P   M   E   E   E   P   A   L   *                       1069

tctgatatttcctgtgtgtgacatcattgtgtatcccccccaccccagtaccctcagacatgtcttgtctgctgcctgggtggcacagattcaatggaacataaacactgggcacaaaat
tctgaacagcagcttcacttgttctttggatggacttgaaagggcattaaagattccttaaacgtaaccgctgtgattctagagttacagtaaaccacgattggaagaaactgcttcca
gcatgcttttaatatgctgggtgacccactcctagacaccaagtttgaactagaaacattcagtacagcactagatattgttaatttcagaagctatgacagccagtgaaattttgggc
aaaacctgagacatagtcattcctgacattctgatcagctttttttggggtaatt
```

*Fig. 2*

*(Part 2 of 2)*

| | Entire Protein | | Catalytic Domain | |
|---|---|---|---|---|
| | Identity (%) | Similarity (%) | Identity (%) | Similarity (%) |
| HDAC9 vs HDAC1 | 26 | 45 | 26 | 45 |
| HDAC9 vs HDAC4 | 56 | 70 | 70 | 83 |
| HDAC9 vs HDAC5 | 57 | 71 | 72 | 84 |
| HDAC9 vs HDAC7 | 43 | 54 | 66 | 77 |
| HDAC9 vs HDAC6 | 17 | 28 | N-term 39 | 56 |
| | | | C-term 44 | 60 |

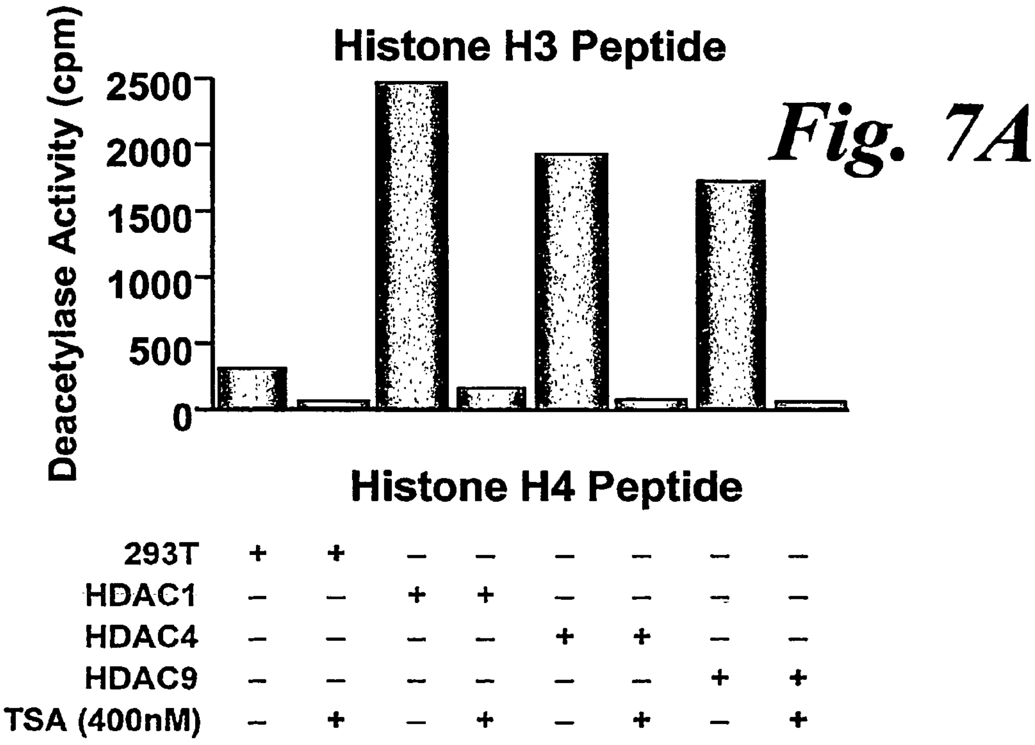
Fig. 7A
Fig. 7B
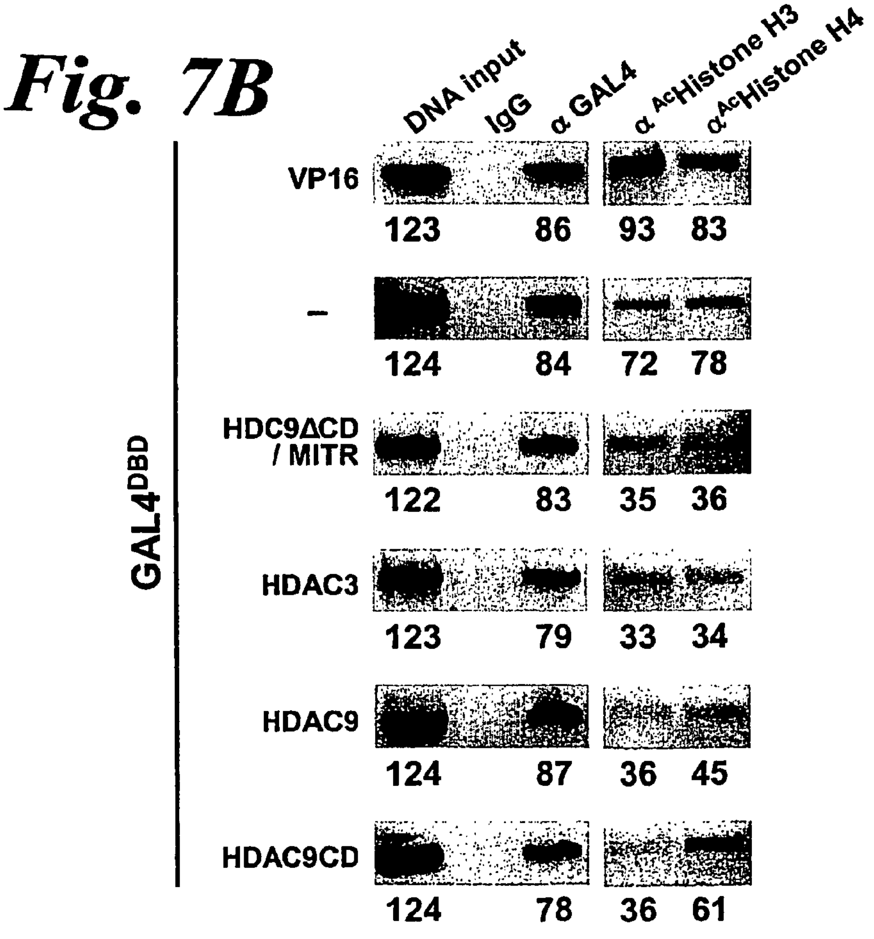

Labels (top to bottom as read): WATER, T47-D, MDA-MB-468, MDA-MB-231, BT-20, Breast, K-562, MONO-MAC-6, NB-4, KG-1, HL-60, REH, NAMALWA, DAUDI, MOLT-3, CD19+ve, Salivery Gland, Placenta, Fetal Liver, Fetal Brain, Testes, Skeletal Muscle, Thymus, Spleen, Bone Marrow, Colon, Lung, Liver, Kidney, Heart, Brain Rows: HDAC9, HDAC9Δ12, HDAC9/HDAC9Δ7, HDAC9Δ12, HDAC9Δ7/Δ12, GAPDH3

HISTONE DEACETYLASE 9

This application is a §371 application of PCT/GB02/04455, which in turn claims priority to GB Application 0123664.5 filed 2 Oct. 2001, the entire disclosure of each of the above-identified applications being incorporated by reference herein.

FIELD OF THE INVENTION

The present invention relates to the identification and isolation of a histone deacetylase and uses of this enzyme. In particular, the present invention relates to histone deacetylase 9 (HDAC9), a member of the class II histone deacetylase family.

BACKGROUND OF THE INVENTION

Eukaryotic DNA is packaged into chromatin in a precise and highly regulated manner. This level of organisation is fundamental to many processes in the cell including replication, repair recombination, chromosomal segregation and transcriptional regulation. DNA is wrapped around the core histone octamer (H2A, H2B, H3 and H4) to form nucleosomes, which are the basic repeating units of chromatin. The crystal structure of the nucleosome has been solved and this has provided much information but there is still a great deal to learn about the mechanisms by which distinct functional domains of chromatin are formed and maintained. The most important changes in chromatin structure are thought to be influenced by post-translational modifications of N-terminal tails of the histones, which protrude from the nucleosome. These are highly basic when unmodified and interact with negatively charged DNA phosphate backbone. Specific amino acids within these tails are targets for a variety enzymes which can produce diverse modifications such as acetylation, methylation, phosphorylation, poly(ADP-ribosylation), and ubiquination. Acetylation is thus far the most widely studied and is catalysed by histone acetyltransferases (HATs) and involves substitution of the $\epsilon$-amino group of specific lysines.

This leads to a more acidic residue and an overall decreased affinity for DNA by the histone octamer. It appears that the histone tails also mediate interactions between nucleosomes to form higher order chromatin structures and they could be disrupted by acetylation. The packaging of DNA into nucleosomal arrays presents a major physical obstacle to the transcriptional machinery when trying to gain access to the DNA template and there is strong evidence that unwinding of nucleosomes due to the acetylation of histone tails plays a fundamental role in the activation of gene transcription. In contrast to histone acetylation in transcriptional activation, enzymes which remove these modifications would be expected to have an important role in down-regulation and gene silencing. This has indeed been shown to be the case and recent studies have also implicated abnormal histone deacetylase function in a number of human cancers.

To date eight histone deacetylases have been characterised which may broadly divided into two related classes which share homology through their deacetylase domains with yeast histone deacetylases Rpd3 and Hda1. Class II HDACs 4, 5 and 7 may be differentiated from the Class I HDACs as they contain an additional N-terminal, non catalytic, region which is homologous to a protein previously characterized as a co-repressor, MEF2-Interacting Transcription Repressor (MITR/HDRP).

Zhou et al (PNAS, 98(19):10572-10577, 2001) purports to disclose the sequence of histone deacetylase HDAC9. However, the protein disclosed in the paper is incomplete and the level of deacetylase activity reported in the paper is below the negative control.

SUMMARY OF THE INVENTION

Broadly, the present invention relates to the identification and cloning of histone deacetylase 9 (HDAC9), and in particular full length HDAC9 polypeptides and HDAC9 polypeptides which have deacetylase activity, and to nucleic acid molecules encoding these polypeptides. The present invention further relates to uses of these polypeptides and nucleic acid molecules, in particular for screening for compounds that are capable of modulating a HDAC9 biological activity.

Accordingly, in a first aspect, the present invention provides an isolated HDAC9 polypeptide having the amino acid sequence set out in FIG. 2. This figure shows the cDNA and predicted amino acid sequence of wild-type histone deacetylase 9 (HDAC9), a 1069 amino acid polypeptide. The HDAC9 sequence is overlaid with the sequence of MITR that shares a common N-terminal amino acid sequence with HDAC9 polypeptide up to amino acid 577 at the end of exon 11, but has a different exon 12. The MITR sequence is a 593 amino acids long.

The HDAC9 sequence reported in Zhou et al (2001) is identical to the sequence shown in FIG. 2 up to amino acid Ser1008, but does not include the C-terminal 61 amino acids which are encoded by exons 24 and 25 as shown in FIG. 2. Significantly, the polypeptide reported in Zhou et al substantially lacks histone deacetylase activity. In contrast, preferred polypeptides of the present invention possess a HDAC9 biological activity, and especially histone deacetylase activity, and include all or part of the amino acid sequence set out between amino acids 1009 and 1069 of FIG. 2. Compared to other histone deacetylases, HDAC9 has 55% sequence identity to HDAC4, 56% sequence identity to HDAC5 and 38% sequence identity to HDAC7.

In a further aspect, the present invention provides an isolated polypeptide having at least 80% amino acid sequence identity with the amino acid sequence set out in FIG. 2. Preferred embodiments of the invention provide isolated polypeptides having at least 95% sequence identity with the sequence set out in FIG. 2.

In a further aspect, the present invention provides an isolated polypeptide which is encoded by a nucleic acid sequence which is capable of hybridising under stringent conditions to the nucleic acid sequence set out in FIG. 2, or a complementary sequence thereof, and in particular to the nucleic acid sequence comprising a sequence which is capable of hybridising to a nucleic acid encoding amino acids 1009 to 1069 of the HDAC9 polypeptide as set out in FIG. 2, or a complementary sequence thereof.

In a further aspect, the present invention provides a substance which is a fragment, active portion or sequence variant of one of the above polypeptides. Preferred fragments and active portions comprise all or part of the HDAC9 sequence set out between amino acids 1009 and 1069 inclusive as shown in FIG. 2. Sequence variants are defined below and include HDAC9 polypeptides in which one or more of the exons shown in FIG. 2 are deleted, such as the variants in which exon 7, exon 12 and/or exon 15 are deleted.

In a further aspect, the present invention provides a HDAC9 polypeptide as defined above joined to a coupling partner.

In a further aspect, the present invention provides an isolated nucleic acid molecule encoding one of the above polypeptides, and complementary nucleic acid sequences thereof. The cDNA sequence of full length HDAC9 is shown in FIG. 2. The present invention also includes nucleic acid molecules having greater than a 90% sequence identity with one of the above nucleic acid sequence. In other embodiments, the present invention relates to nucleic acid sequences which hybridise to the coding sequence set out in FIG. 2, or a complementary sequence thereof, and more especially to nucleic acid sequences which hybridise to a nucleic acid sequence encoding amino acids 1009 to 1069 as set out in FIG. 2, or a complementary sequence thereof.

In further aspects, the present invention provides an expression vector comprising one of the above nucleic acid operably linked to control sequences to direct its expression, and host cells transformed with the vectors. The present invention also includes a method of producing a histone deacetylase 9 polypeptide, or a fragment or active portion thereof, comprising culturing the host cells and isolating the polypeptide thus produced.

In a further aspect, the present invention provides a composition comprising one or more of the above polypeptides or nucleic acid molecules as defined herein.

In a further aspect, the present invention provides the use of a histone deacetylase 9 polypeptide as defined herein (including fragments, active portions or sequence variants), or a corresponding nucleic acid molecule, for screening for candidate compounds which (a) share a histone deacetylase 9 biological activity or (b) bind to the histone deacetylase 9 polypeptide or (c) inhibit a biological activity of a histone deacetylase 9 polypeptide. By way of example, screening can be carried out to find peptidyl or non-peptidyl mimetics or inhibitors of the HDAC9 polypeptides to develop as lead compounds in pharmaceutical research.

Thus, in one embodiment, the present invention provides a method of identifying a compound which is capable of modulating an activity of a histone deacetylase 9 polypeptide, the method comprising:

(a) contacting at least one candidate compound with a histone deacetylase 9 (HDAC9) polypeptide as defined herein under conditions in which the candidate compound and HDAC9 polypeptide are capable of interacting;
(b) determining in an assay for a HDAC9 activity whether the candidate compound modulates the activity; and,
(c) selecting a candidate compound which modulates an activity of the HDAC9 polypeptide.

In a further aspect, the present invention provides a method of identifying a compound which is capable of inhibiting histone deacetylase 9 (HDAC9) polypeptide, the method comprising:

(a) contacting at least one candidate compound and a HDAC9 polypeptide as defined herein in the presence of a substrate for HDAC9 under conditions in which the candidate compound, HDAC9 polypeptide and HDAC9 substrate are capable of interacting;
(b) determining whether the candidate compound inhibits the activity of the HDAC9 polypeptide in reacting with the substrate; and,
(c) selecting the candidate compound which inhibits the activity of the HDAC9 polypeptide on the substrate.

In one embodiment, the substrate is a histone which is a substrate for HDAC9. In this assay, the effect of a candidate compound in modulating the activity of HDAC9 can be assessed by determining the amounts of acetylated and deacetylated histone present after the reaction of HDAC9 in the presence or absence of the candidate compounds. This can readily be determined using techniques well known in the art, for example employing antibodies which are capable of specifically binding to acetylated or deacetylated substrate.

In this aspect of the invention, preferably the activity of the HDAC9 polypeptide is the activity of removing an acetyl groups from the substrate. Conveniently, the progress of this reaction can be assessed by labelling the substrate with a detectable label (e.g. a radioactive label) and measuring the amount of label released from the substrate by the action of the HDAC9 polypeptide, e.g. in a scintillation proximity assay. Preferably, the method is for screening for modulators of HDAC9 which may be useful in for the treatment of cancer.

In a further aspect, the present invention provides a method of identifying a compound which is capable of inhibiting histone deacetylase 9 (HDAC9) polypeptide, the method comprising:

(a) contacting at least one candidate compound and a HDAC9 polypeptide as defined herein in the presence of a substrate for HDAC9 under conditions in which the candidate compound, HDAC9 polypeptide and HDAC9 substrate are capable of interacting;
(b) determining whether the candidate compound inhibits the activity of the HDAC9 polypeptide in reacting with the substrate; and,
(c) selecting the candidate compound which inhibits the activity of the HDAC9 polypeptide on the substrate.

In one embodiment, candidate compounds are screened for activity in modulating HDAC9 in a cell based reporter assay using cells which produce HDAC9 fused to a nucleic acid binding domain such as GAL4, e.g. by transfecting cells with appropriate expression and reporter vectors. In the cells, HDAC9-GAL4 chimeric protein which is capable of interacting with a GAL4 DNA binding site can bind to a promoter which includes such a site, the promoter being linked to a reporter construct. The HDAC9 activity can thus deacetylate core histones associated with a DNA surrounding GAL4 binding site resulting in down regulation of promoter activity. Compounds that inhibit HDAC9 activity would counteract this down regulation. Therefore, changes in reporter activity can be used as a screen for compounds that either stimulate or inhibit HDAC9 activity.

In a further aspect, the present invention provides antibodies capable of specifically binding to the above HDAC9 polypeptides, or an active portion, domain or fragment thereof, and the use of the HDAC9 polypeptide or peptides based on the sequence for designing antibodies or for use in a method of preparing antibodies capable of binding to HDAC9. These antibodies can be used in assays to detect and quantify the presence of HDAC9 polypeptide, in methods of purifying HDAC9 polypeptides, and as inhibitors of HDAC9 polypeptides.

In a further aspect, the present invention provides a method of amplifying a nucleic acid test sample comprising priming a nucleic acid polymerase reaction with nucleic acid encoding a HDAC9 polypeptide as defined above.

In a further aspect, the present invention provides a method for the diagnosis or prognosis of cancer, the method comprising determining the presence or amount of HDAC9 polypeptide, or an isoform thereof, or HDAC9 nucleic acid in a sample from a patient. This is discussed in more detail below.

These and other aspects of the present invention are described in more detail below. By way of example and not limitation, embodiments of the present invention will now be described in more detail with reference to the accompanying figures.

A. Amino acid sequence alignment of HDAC9 (SEQ ID NO: 2), HDAC4 (SEQ ID NO: 70), HIDAC5 (SEQ ID NO: 71), HDAC7 (SEQ ID NO: 72), and a bacterial deacetylase, HDLP (SEQ ID NO: 69). The indicated sequences were aligned using Clustal W. Identical residues are boxed and highlighted in dark grey; similar residues are shaded in light grey.

B. Evaluation of amino acid identities and similarities of HDAC9 compared with other histone deacetylases. Values were obtained by comparing the whole protein or deacetylase domain of HDAC9 with the indicated protein sequences on BioEdit Sequence Alignment Editor using the Blosum62 matrix.

C. Phylogenetic tree of HDAC1 through to HDAC9. Sequences were aligned using the Clustal W server at the Centre for Molecular and Biomolecular Informatics (University of Nijmegen). The PHYLIP (bracket) notation output was used to construct an unrooted tree.

Figure 5:
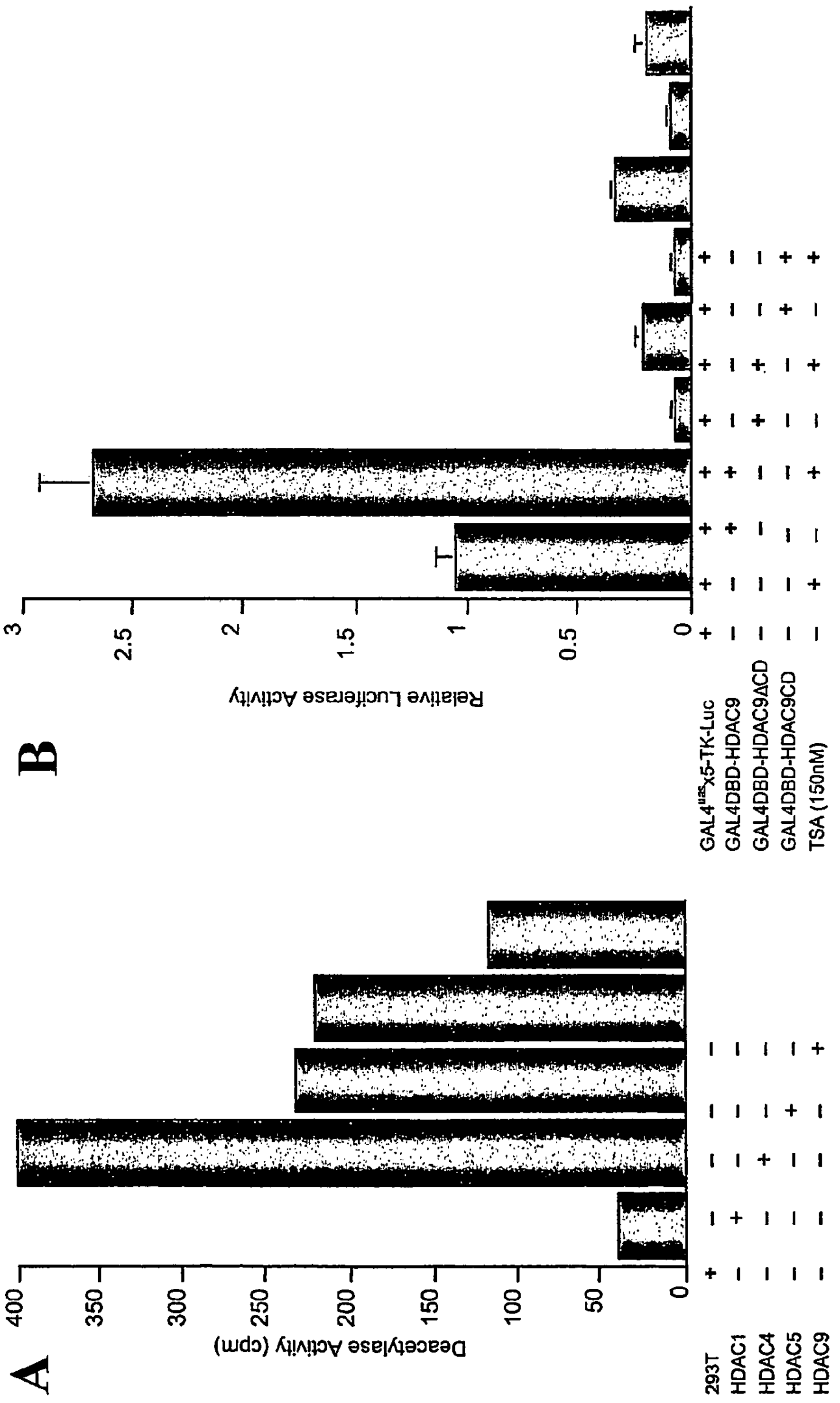

FIG. 5. HDAC9 possesses HDAC activity and represses basal transcription.

A. HDAC9 deacetylates histone H4 peptide. 293T cells were transfected with FLAG-tagged HDAC. Whole cell lysates were produced and the HDACs precipitated with anti-FLAG agarose. The beads were assayed for their ability to deacetylate a [$^3$H]acetyl-labelled peptide corresponding to the N-Terminus of histone H4. Free acetate was extracted and measured by scintillation counting.

B. GAL4-HDAC9 Inhibits promoter activity in-vivo in a TSA sensitive manner. GAL4-Tk-Luc was transiently transfected into 293T cells together with 100 ng GAL4 DBD fusions. All Results were performed in duplicate and error.

Figure 6:
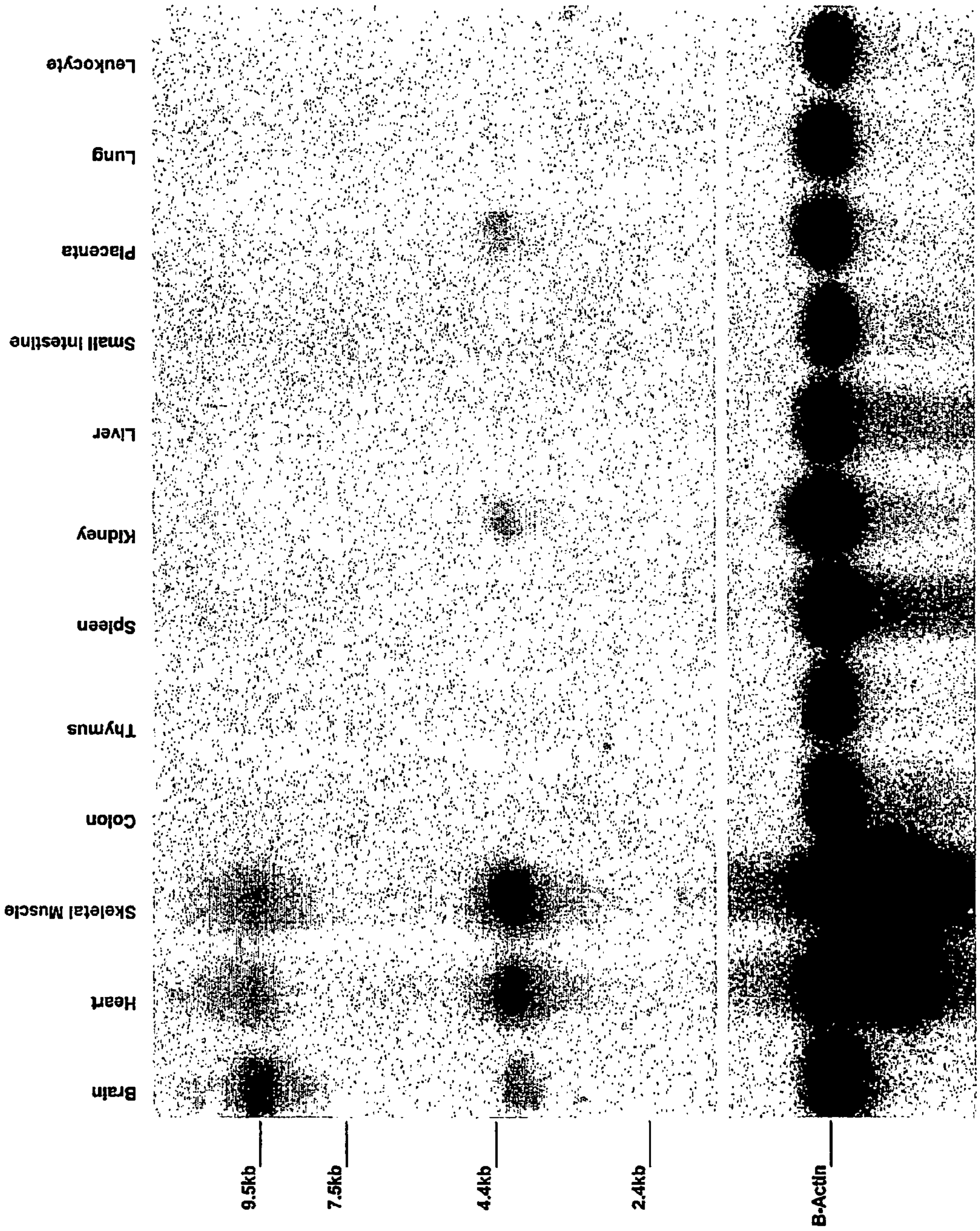

FIG. 6. Northern blot showing the differential expression of HDAC9 polypeptide in human tissues. A multiple human tissue Northern Blot was analysed with a $^{32}$P labelled probe corresponding to the sequence found only in the full length HDAC9 cDNA in order to evaluate levels of expression of HDAC9 mRNA. The blot was reprobed with β-actin cDNA as a normalisation control. The tissues examined are indicated at the top of each lane. Positions of the RNA size markers are indicated in kilobases on the left of the blot.

FIG. 7. HDAC9 displays higher activity towards histone H3 peptide. 293T cells were transfected with FLAG-tagged HDAC. Whole cell lysates were produced and the HDACs precipitated with anti-FLAG agarose. The beads were assayed for their ability to deacetylate a [$^3$H]acetyl-labelled peptide corresponding to the N-Terminus of Histone H3. Free acetate was extracted and measured by scintillation counting.

FIG. 8. Expression of various HDAC9 isoforms in normal and cancer cells. Total RNA was isolated from the indicated cell lines and tissues and cDNA generated with M-MLV reverse transcriptase using either gene specific or random primers. Standard PCR was performed for 32 cycles.

Figure 9:
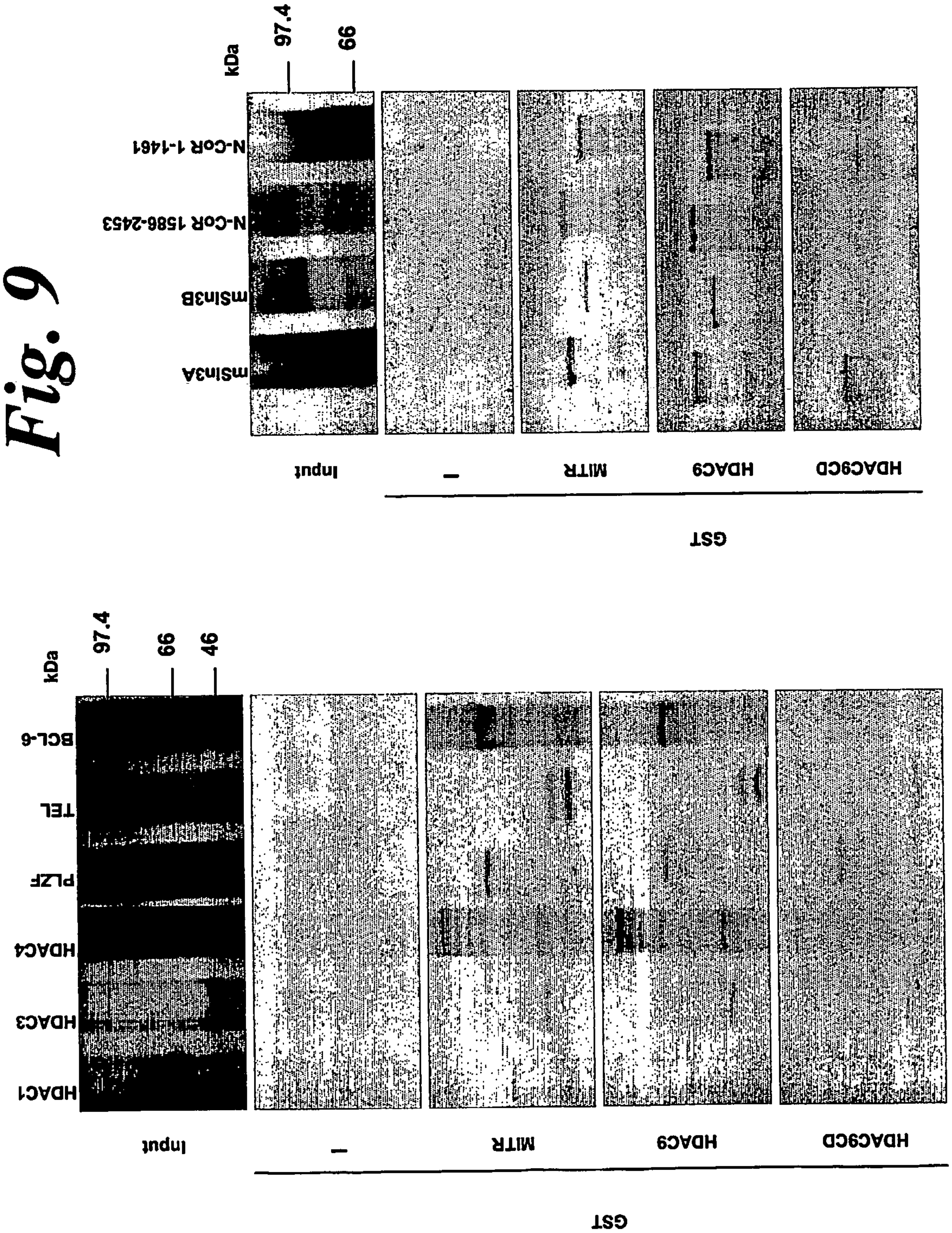

FIG. 9. In vitro interactions of HDAC9 with various oncoproteins and co-repressors GST-HDAC9, GST-HDAC9CD and GST-MITR were produced from *E. coli* DH5α. [$^{35}$S] methionine-labeled proteins were synthesized in-vitro using a rabbit reticulocyte lysate-coupled transcription-translation system. Assays were performed in NETN Buffer, washed in H Buffer, separated by SDS-PAGE and visualised by autoradiography.

Figure 10:
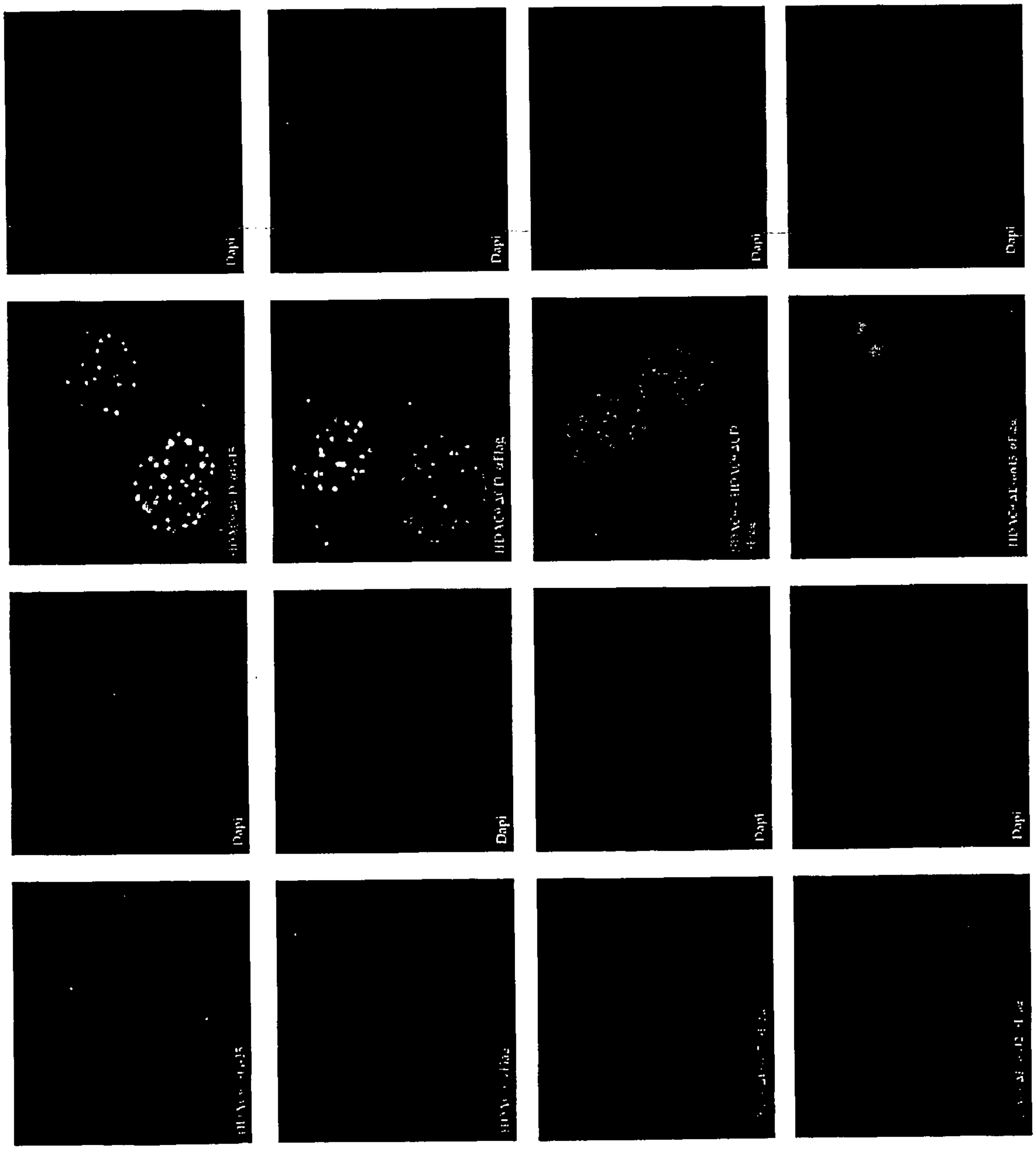

FIG. 10. Cellular localization of various isoforms of HDAC9. COS-1 cells were transiently transfected with N-Terminus flag tagged HDAC9, HDAC9ΔCD/MITR, HDAC9ΔExon7, HDAC9 ΔExon12 or HDAC9ΔExon15 as indicated. After methanol fixation, cells were stained with dapi (blue) and antibodies raised against HDAC9 or flag (green). G-15 is an antibody to the N-Terminus of HDAC9 which h detects all isoforms (including HDAC9ΔCD/MITR).

Figure 11:
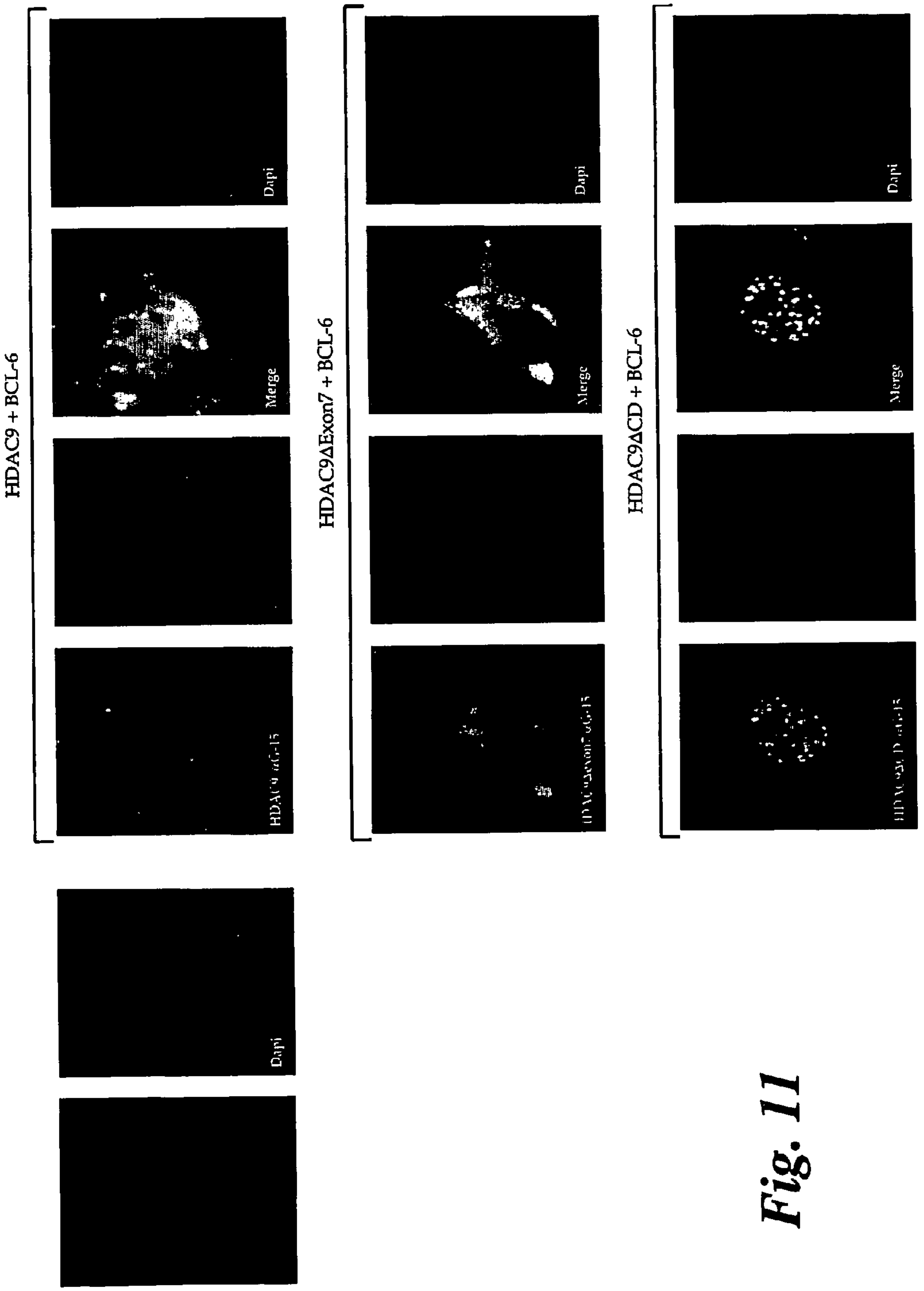

FIG. 11. Effect of various isoforms of HDAC9 on the cellular localization of BCL-6. COS-1 cells were transiently transfected with N-Terminus flag tagged HDAC9, HDAC9ΔCD, or HDAC9Δexon7, as indicated. After methanol fixation, cells were stained with dapi (blue) and antibodies raised against HDAC9 G-15 (green) or BCL-6(red).

Figure 12:
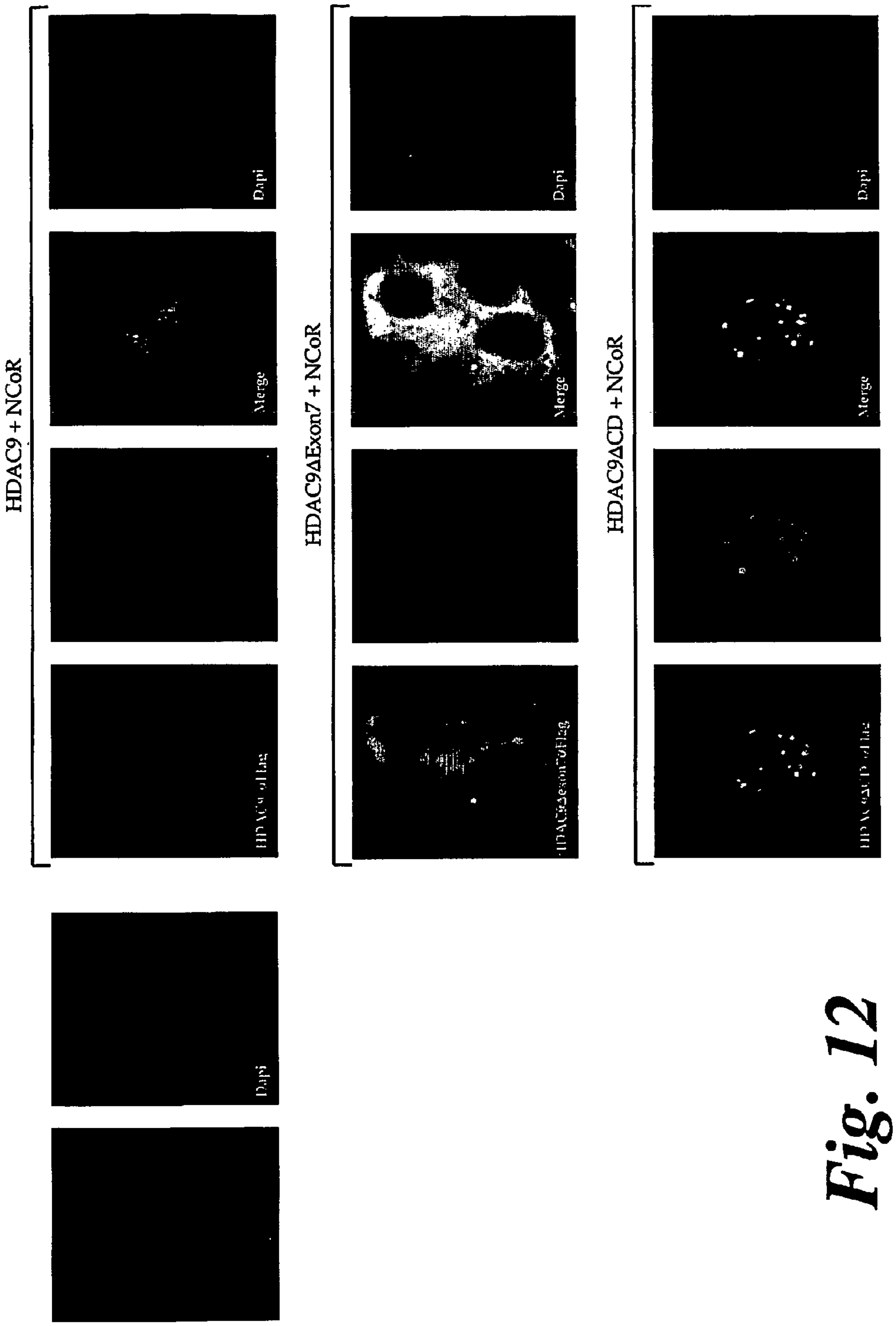

FIG. 12. Effect of various isoforms of HDAC9 on the cellular localization of NCoR. COS-1 cells were transiently transfected with N-Terminus flag tagged HDAC9, HDAC9ΔCD, or HDAC9Δexon7, as indicated After methanol fixation, cells were stained with dapi (blue) and antibodies raised against FLAG (green) G-15 or NCoR (red).

Figure 13:
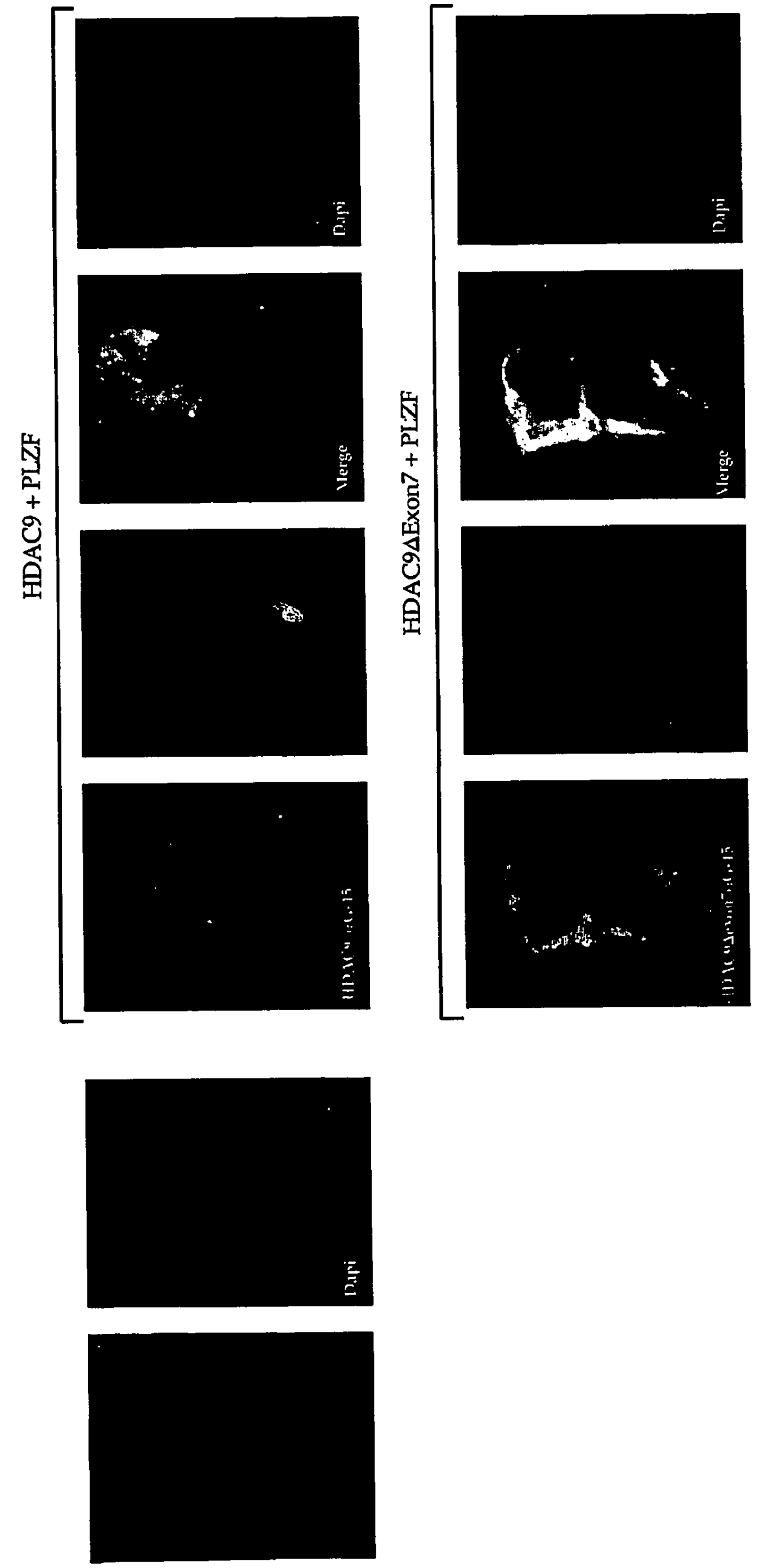

FIG. 13. Effect of various isoforms of HDAC9 on the cellular localization of PLZF. COS-1 cells were transiently transfected with N-Terminus flag tagged HDAC9, or HDAC9 Δexon7, as indicated After methanol fixation, cells were stained with dapi (blue) and antibodies raised against HDAC9 G-15 (green) or PLZF (red).

Histone Deacetylase 9 Nucleic Acid

Figure 2:
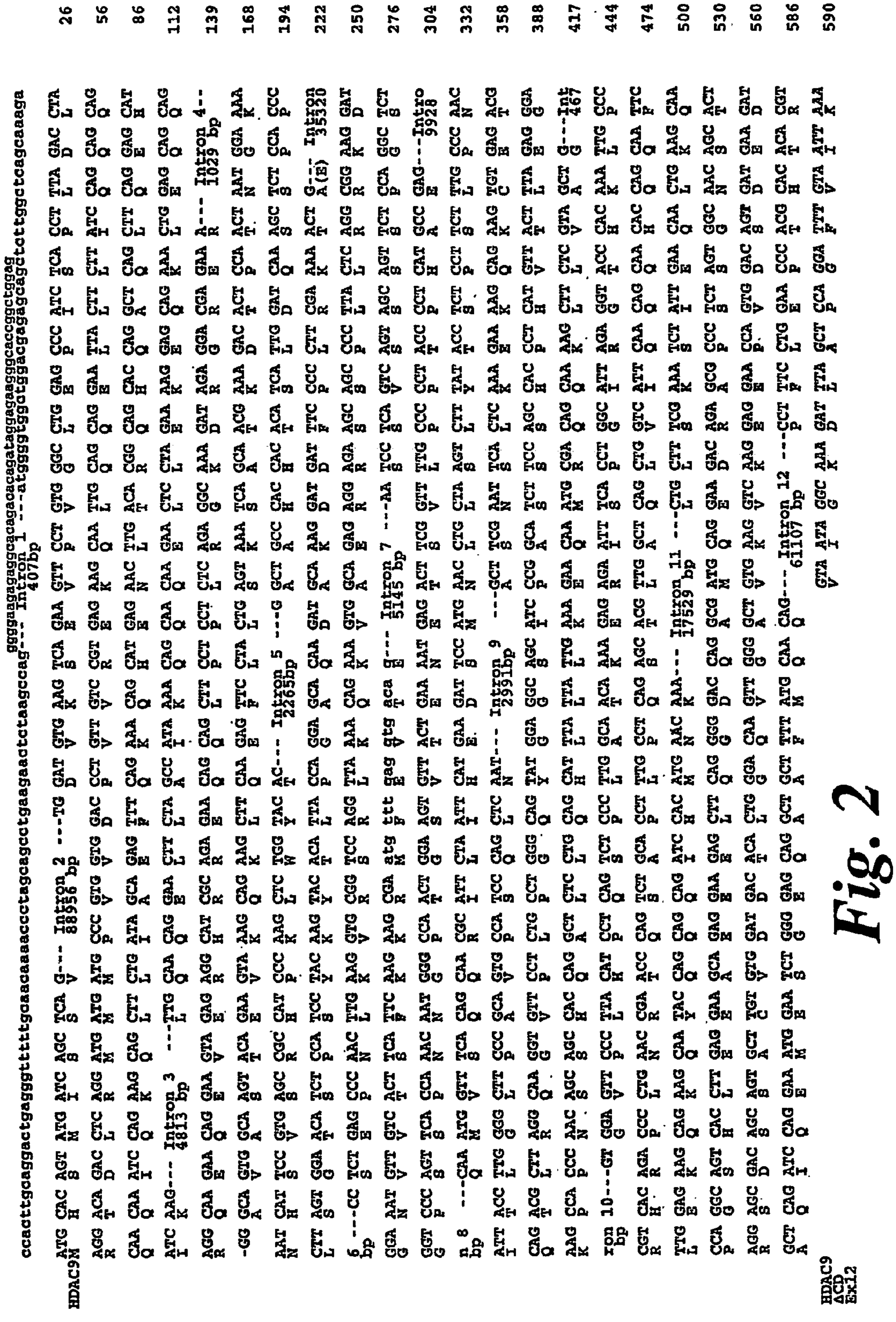
FIG. 2. HDAC9 cDNA sequence together with the predicted HDAC9 amino acid sequence (SEQ ID NO: 1). HDAC9 full length cDNA has an open reading frame of 3207 bp which yields a 1069 amino acids protein. The HDAC9Δexon7 isoform results in an A to E substitution at position 222. The sequence specific to HDAC9ΔCD exon 12 is shown in italics (SEQ ID NOs: 3 and 4).

A "HDAC9 nucleic acid" includes a nucleic acid molecule which has a nucleotide sequence encoding a polypeptide comprising the amino acid sequence shown in FIG. 2 or any one of the other HDAC9 polypeptides of the present invention. The HDAC9 coding sequence may be the full length nucleic acid sequence shown in FIG. 2, a complementary nucleic acid sequence, or it may be a sequence variant differing from one of the above sequences by one or more of addition, insertion, deletion and substitution of one or more nucleotides of the sequence shown. Changes to a nucleotide sequence may result in an amino acid change at the protein level, or not, as determined by the genetic code. Nucleic acid encoding a polypeptide which is a sequence variant preferably has at least 80% sequence identity, more preferably at least 95% sequence identity, more preferably at least 98% sequence identity, and most preferably at least 99% sequence identity with the nucleic acid sequence shown in FIG. 2.

The present invention also includes fragments of the HDAC9 nucleic acid sequences described herein, the fragments preferably being at least 60, 120, 180, 240, 480 or 960 nucleotides in length. Preferred HDAC9 nucleic acid fragments share at least part of their nucleic acid sequence with the HDAC9 nucleic acid sequence which encodes amino acids 1008 to 1069 of the polypeptide shown in FIG. 2, or a complementary sequence thereof.

Generally, nucleic acid according to the present invention is provided as an isolate, in isolated and/or purified form, or free or substantially free of material with which it is naturally associated. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

The present invention also includes nucleic acid molecules which are capable of hybridising to one of the HDAC9 sequences disclosed herein, or a complementary sequence thereof. Stringency of hybridisation reactions is readily determinable by one of ordinary skill in the art, and generally is an empirical calculation dependent upon probe length, washing temperature and salt concentration. In general, longer probes require higher temperatures for proper annealing, while shorter probes need lower temperatures. Hybridisation generally depends on the ability of denatured DNA to reanneal when complementary strands are present in an environment below their melting temperature. The higher the degree of desired homology between the probe and hybridisable sequence, the higher the relative temperature which can be used. As a result, it follows that higher relative temperatures would tend to make the reaction conditions more stringent, while lower temperatures less so. For additional details and explanation of stringency of hybridisation reactions, see Ausubel et al, Current Protocols in Molecular Biology, Wiley Interscience Publishers, (1995).

Preferably, a nucleic acid sequence will hybridise to a HDAC9 sequence of the invention, or a complementary sequence thereof under "stringent conditions". These are well known to those skilled in the art and include those that: (1) employ low ionic strength and high temperature for washing, for example 0.015 M sodium chloride/0.0015 M sodium citrate/0.1% sodium dodecyl sulfate at 50° C.; (2) employ during hybridisation a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 760 mM sodium chloride, 75 mM sodium citrate at 42° C.; or (3) employ 50% formamide, 5×SSC (0.75 M NaCl, 0.075 M sodium citrate), 50 mM sodium phosphate (pH 6 8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

Nucleic acid sequences encoding all or part of the HDAC9 gene and/or its regulatory elements can be readily prepared by the skilled person using the information and references contained herein and techniques known in the art (for example, see Sambrook, Fritsch and Maniatis, Molecular Cloning, A Laboratory Manual, Cold Spring Harbour Laboratory Press, 1989, and Ausubel et al, Short Protocols in Molecular Biology, John Wiley and Sons, 1992). These techniques include (i) the use of the polymerase chain reaction (PCR) to amplify samples of such nucleic acid, e.g. from genomic sources, (ii) chemical synthesis, or (iii) amplification in *E. coli*. Modifications to the HDAC9 sequences can be made, e.g. using site directed mutagenesis, to provide expression of modified HDAC9 polypeptide or to take account of codon preference in the host cells used to express the nucleic acid.

PCR techniques for the amplification of nucleic acid are described in U.S. Pat. No. 4,683,195. The HDAC9 nucleic acid sequences provided herein readily allow the skilled person to design PCR primers. References for the general use of PCR techniques include Mullis et al, Cold Spring Harbour Symp. Quant. Biol., 51:263, (1987), Ehrlich (ed), PCR Technology, Stockton Press, NY, 1989, Ehrlich et al, Science, 252:1643-1650, (1991), "PCR protocols; A Guide to Methods and Applications", Eds. Innis et al, Academic Press, New York, (1990).

In order to obtain expression of the HDAC9 nucleic acid sequences, the sequences can be incorporated in a vector having control sequences operably linked to the HADC9 nucleic acid to control its expression. The vectors may include other sequences such as promoters or enhancers to drive the expression of the inserted nucleic acid, nucleic acid sequences so that the HDAC9 polypeptide is produced as a fusion and/or nucleic acid encoding secretion signals so that the polypeptide produced in the host cell is secreted from the cell. Suitable vectors can be chosen or constructed, containing appropriate regulatory sequences, including promoter sequences, terminator fragments, polyadenylation sequences, enhancer sequences, marker genes and other sequences as appropriate. Vectors may be plasmids or viral, e.g. 'phage, or phagemid, as appropriate. For further details see, for example, Molecular Cloning: a Laboratory Manual: 2nd edition, Sambrook et al., 1989, Cold Spring Harbour Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

HDAC9 polypeptide can be obtained by transforming the vectors into host cells in which the vector is functional, culturing the host cells so that the HDAC9 polypeptide is produced and recovering the HDAC9 polypeptide from the host cells or the surrounding medium. Prokaryotic and eukaryotic cells are used for this purpose in the art, including strains of *E. coli*, insect cells (e.g. transformed with baculovirus), yeast, and eukaryotic cells such as COS or CHO cells. The choice of host cell can be used to control the properties of the HDAC9 polypeptide expressed in those cells, e.g. controlling where the polypeptide is deposited in the host cells or affecting properties such as its glycosylation and phosphorylation. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components such as a carrier. Polypeptides may also be expressed in in vitro systems, such as reticulocyte lysate.

The nucleic acid sequences provided herein are useful for identifying HDAC9 nucleic acid in a test sample. The present invention provides a method of obtaining nucleic acid of interest, the method including hybridising a probe sharing all or part of the sequence provided herein, or a complementary sequence, to the target nucleic acid. Hybridisation is generally followed by identification of successful hybridisation and isolation of nucleic acid which has hybridised to the probe, which may involve one or more steps of PCR. These methods may be useful in determining whether HDAC9 nucleic acid is present in a sample, e.g. in a particular type of cells present in the sample.

Nucleic acid according to the present invention is obtainable using one or more oligonucleotide probes or primers designed to hybridise with one or more fragments of the nucleic acid sequence shown herein, particularly fragments of relatively rare sequence, based on codon usage or statistical analysis. A primer designed to hybridise with a fragment of the nucleic acid sequence shown in the above figures may be used in conjunction with one or more oligonucleotides designed to hybridise to a sequence in a cloning vector within which target nucleic acid has been cloned, or in so-called "RACE" (rapid amplification of cDNA ends) in which cDNA's in a library are ligated to an oligonucleotide linker and PCR is performed using a primer which hybridises with the sequence shown herein and a primer which hybridises to the oligonucleotide linker.

On the basis of amino acid sequence information, oligonucleotide probes or primers may be designed, taking into account the degeneracy of the genetic code, and where appropriate, codon usage of the organism from the candidate nucleic acid is derived. An oligonucleotide for use in nucleic acid amplification may have about 10 or fewer codons (e.g. 6, 7 or 8), i.e. be about 30 or fewer nucleotides in length (e.g. 18, 21 or 24).

Generally specific primers are upwards of 14 nucleotides in length, but not more than 18-20. Those skilled in the art are well versed in the design of primers for use processes such as PCR.

Accordingly, a further aspect of the present invention provides an oligonucleotide or nucleotide fragment of the one of the nucleotide sequence disclosed herein, or a complementary sequence, in particular for use in a method of obtaining and/or screening nucleic acid. The sequences referred to above may be modified by addition, substitution, insertion or deletion of one or more nucleotides, but preferably without abolition of ability to hybridise selectively with nucleic acid with the sequence shown herein, that is wherein the degree of sequence identity of the oligonucleotide or polynucleotide with one of the sequences given is sufficiently high.

In some preferred embodiments, oligonucleotides according to the present invention that are fragments of any of the nucleic acid sequences provided herein, or complementary sequences thereof, are at least about 10 nucleotides in length, more preferably at least about 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence of HDAC9 nucleic acid in a test sample.

HDAC9 Polypeptides

The HDAC9 polypeptides disclosed herein, or fragments or active portions thereof, can be used as pharmaceuticals, in the developments of drugs, for further study into its properties and role in vivo and to screen for HDAC9 inhibitors. Thus, a further aspect of the present invention provides a polypeptide which has the amino acid sequence shown in FIG. 2, which may be in isolated and/or purified form, free or substantially free of material with which it is naturally associated, such as polypeptides other than HDAC9.

The present invention also includes active portions, domains and fragments (including domains) of the HDAC9 polypeptides of the invention.

An "active portion" of HDAC9 polypeptide means a peptide which is less than said full length HDAC9 polypeptide, but which retains at least some of its essential biological activity, e.g. as a deacetylase. Active portions may be great than 100 amino acids, more preferably greater than 200 amino acids, more preferably greater than 300 amino acids and most preferably greater than 400 amino acids in length. Preferred active portion include all or part of the 61 C-terminal amino acids shown in FIG. 2.

A "fragment" of the HDAC9 polypeptide means a stretch of amino acid residues of at least 5 contiguous amino acids from the sequences set out as FIG. 2, or more preferably at least 7 contiguous amino acids, or more preferably at least 10 contiguous amino acids or more preferably at least 20 contiguous amino acids or more preferably at least 40 contiguous amino acids. Fragments of the HDAC9 polypeptide sequences may be useful as antigenic determinants or epitopes for raising antibodies to a portion of the HDAC9 amino acid sequence which also forms part of the present invention. For instance, fragments of HDAC9 can act as sequestrators or competitive antagonists by interacting with other proteins, e.g. if they possess a protein interaction domain present in the full length HDAC9 sequence.

Polypeptides which are amino acid sequence variants are also provided by the present invention. A "sequence variant" of the HDAC9 polypeptide, or an active portion or fragment thereof, means a polypeptide modified by varying the amino acid sequence of the protein, e.g. by manipulation of the nucleic acid encoding the protein or by altering the protein itself. Such sequence variants of the natural amino acid sequence may involve insertion, addition, deletion or substitution of one, two, three, five, ten, twenty or more amino acids.

Preferred polypeptides have HDAC9 biological activity, that is, they are capable of removing an acetyl group from a substrate such as a histone (e.g. histone H3 or H4). HDAC9 and isoforms of the protein may have other activities and one potential role is linked with the Δexon7 isoform. It has been suggested that HDACs can function as molecular reservoirs within the cell as well as deacetylating histones, and also as transcription factors. We have observed that HDAC9 interacts in vitro and co-localizes in vivo with a number of transcriptional repressors, such as TEL, PLZF and BCL-6, whose function has been implicated in the pathogenesis of hematological malignancies, as well as the co-repressors mSIN3A/B and NCoR. When HDAC9 or HDAC9Δexon7 are co-transfected into COS cells they have the ability to delocalize BCL-6 and PLZF. NCoR is also delocalised. The interesting aspect of these interactions is that HDAC9 is located in the nucleus whilst HDAC9Δexon7 is cytoplasmic. Additionally, the HDAC9ΔCD/hMITR isoform displays a microspeckled distribution within the nucleus which is distinct to that of HDAC9.

Preferably, a polypeptide which is an amino acid sequence variant of the amino acid sequence shown in FIG. 2 at least 80% sequence identity, more preferably at least 90% sequence identity, more preferably at least 95% sequence identity, more preferably at least 97% sequence identity more preferably at least 98% sequence identity and most preferably at least 99% sequence identity to the sequences of FIG. 2.

The skilled person can readily make sequence comparisons and determine identity using techniques well known in the art, e.g. using the GCG program which is available from Genetics Computer Group, Oxford Molecular Group, Madison, Wis., USA, Version 9.1. Particular amino acid sequence variants may differ from those shown in SEQ ID Nos: 2 or 4 by insertion, addition, substitution or deletion of 1 amino acid, 2, 3, 4, 5-10, 10-20 20-30, 30-50, 50-100, 100-150, or more than 150 amino acids.

"Percent (%) amino acid sequence identity" with respect to the HDAC9 polypeptide sequences identified herein is defined as the percentage of amino acid residues in a candidate sequence that are identical with the amino acid residues in the HDAC9 sequence, after aligning the sequences and introducing gaps, if necessary, to achieve the maximum percent sequence identity, and not considering any conservative substitutions as part of the sequence identity. The % identity values can be generated by WU-BLAST-2 which was obtained from [Altschul et al, Methods in Enzymology, 266:460-480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold(T) =11. The HSPS and HSPS2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Similarly, "percent (%) nucleic acid sequence identity" with respect to the coding sequence of the HDAC9 polypeptides identified herein is defined as the percentage of nucleotide residues in a candidate sequence that are identical with the nucleotide residues in the HDAC9 coding sequence as provided in FIG. 2. The identity values used herein were generated by the BLASTN module of WU BLAST-2 set to the default parameters, with overlap span and overlap fraction set to 1 and 0.125, respectively.

A polypeptide according to the present invention may be isolated and/or purified (e.g. using an antibody) for instance after production by expression from encoding nucleic acid. Polypeptides according to the present invention may also be generated wholly or partly by chemical synthesis. The isolated and/or purified polypeptide may be used in formulation of a composition, which may include at least one additional component.

The HDAC9 polypeptides can also be linked to a coupling partner, e.g. an effector molecule, a label, a drug, a toxin and/or a carrier or transport molecule. Techniques for coupling the peptides of the invention to both peptidyl and non-peptidyl coupling partners are well known in the art.

Antibodies Capable of Binding HDAC9 Polypeptides

A further important use of the HDAC9 polypeptides is in raising antibodies that have the property of specifically binding to the HDAC9 polypeptides or fragments thereof. The techniques for producing monoclonal antibodies to HDAC9 protein are well established in the art. Preferred antibodies are capable of specifically binding to an epitope of HDAC9 located or partially located between amino acids 1009 and 1069 of the amino acid sequence shown in FIG. 2. The anti-HDAC9 antibodies of the present invention may be specific in the sense of being able to distinguish between the polypeptide it is able to bind and other human polypeptides for which it has no or substantially no binding affinity (e.g. a binding affinity of about 1000× worse). Specific antibodies bind an epitope on the molecule which is either not present or is not accessible on other molecules. Other preferred antibodies include those capable of substantially neutralising a HDAC9 biological activity and especially biological activity as a histone deacetylase.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357: 80-82, 1992). Isolation of antibodies and/or antibody-producing cells from an animal may be accompanied by a step of sacrificing the animal. As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways that are well known in the art. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope. Humanised antibodies in which CDRs from a non-human source are grafted onto human framework regions, typically with the alteration of some of the framework amino acid residues, to provide antibodies which are less immunogenic than the parent non-human antibodies, are also included within the present invention.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2 188 638 A or EP 0 239 400 A. Cloning and expression of chimeric antibodies are described in EP 0 120 694 A and EP 0 125 023 A.

In a further aspect the present invention provides a method of making antibodies, the method comprising employing a HDAC9 polypeptide or a fragment thereof as an immunogen. The present invention also provides a method of screening for antibodies which are capable of specifically binding HDAC9 polypeptide, the method comprising contacting a HDAC9 polypeptide with one or more candidate antibodies and detecting whether binding occurs.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule. One favoured mode is by covalent linkage of each antibody with an individual fluorochrome, phosphor or laser exciting dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

Antibodies according to the present invention may be used in screening for the presence of a polypeptide, for example in a test sample containing cells or cell lysate as discussed, and may be used in purifying and/or isolating a polypeptide according to the present invention, for instance following production of the polypeptide by expression from encoding nucleic acid. Antibodies may modulate the activity of the polypeptide to which they bind and so, if that polypeptide has a deleterious effect in an individual, may be useful in a therapeutic context (which may include prophylaxis).

Screening for Mimetic Substances

The present invention further relates to the use of a histone deacetylase 9 polypeptide or nucleic acid molecule for screening for candidate compounds which (a) share a histone deacetylase 9 biological activity or (b) bind to the histone deacetylase 9 polypeptide or (c) inhibit a biological activity of a histone deacetylase 9 polypeptide.

It is well known that pharmaceutical research leading to the identification of a new drug may involve the screening of very large numbers of candidate substances, both before and even after a lead compound has been found. This is one factor which makes pharmaceutical research very expensive and time-consuming. Means for assisting in the screening process can have considerable commercial importance and utility.

By way of example, screening can be carried out to find peptidyl or non-peptidyl mimetics or inhibitors of the HDAC9 polypeptides to develop as lead compounds in pharmaceutical research.

In this aspect of the invention, preferably the activity of the HDAC9 polypeptide is the activity of removing an acetyl groups from the substrate. Conveniently, the progress of this reaction can be assessed by labelling the substrate with a detectable label (e.g. a radioactive label) and measuring the amount of label released from the substrate by the action of the HDAC9 polypeptide, e.g. in a scintillation proximity assay. Preferably, the method is for screening for modulators of HDAC9 which may be further tested for use a therapeutic, especially for the treatment of cancer.

A method of screening for a substance which modulates activity of a polypeptide may include contacting one or more test substances with a HDAC9 in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Combinatorial library technology provides an efficient way of testing a potentially vast number of different substances for ability to modulate activity of a polypeptide. Such libraries and their use are known in the art. The use of peptide libraries is preferred.

Prior to or as well as being screened for modulation of activity, test substances may be screened for ability to interact with the polypeptide, e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide. Alternatively, the screen could be used to screen test substances for binding to a HDAC9 specific binding partner, to find mimetics of the HDAC9 polypeptide, e.g. for testing as therapeutics.

In one embodiment, the present invention provides a method of identifying a compound which is capable of modulating an activity of a histone deacetylase 9 polypeptide, the method comprising:

(a) contacting at least one candidate compound with a histone deacetylase 9 (HDAC9) polypeptide as defined herein under conditions in which the candidate compound and HDAC9 polypeptide are capable of interacting;

(b) determining in an assay for a HDAC9 activity whether the candidate compound modulates the activity; and (c) selecting a candidate compound which modulates an activity of the HDAC9 polypeptide.

In a preferred embodiment, the present invention provides a method of identifying a compound which is capable of inhibiting histone deacetylase 9 (HDAC9) polypeptide, the method comprising:

(a) contacting at least one candidate compound and a HDAC9 polypeptide as defined herein in the presence of a substrate for HDAC 9 under conditions in which the candidate compound, HDAC9 polypeptide and HDAC9 substrate are capable of interacting;

(b) determining whether the candidate compound inhibits the activity of the HDAC9 polypeptide in reacting with the substrate; and, (c) selecting the candidate compound which inhibits the activity of the HDAC9 polypeptide on the substrate.

Following identification of a candidate compound which modulates or inhibits HDAC9 activity, the substance may be investigated further. Furthermore, it may be manufactured and/or used in preparation, i.e. manufacture or formulation, of a composition such as a medicament, pharmaceutical composition or drug.

Diagnostic Methods

Recent studies have implicated abnormal histone deacetylase function with a number of human cancers. Accordingly, the present invention also provides the use of HDAC9 as a diagnostic marker for cancer, e.g. by correlating this level with the amount of the HDAC9 polypeptide, an isoform thereof, or HDAC9 nucleic acid present in a control.

Under normal circumstances, the expression of HDAC9 isoforms which contain the catalytic domain appears to be tightly regulated, with the protein only found at high levels in adult and foetal brain, and to a lesser extent skeletal muscle, testes, bone marrow, thymus, spleen, $CD14^{+ve}$, and $CD19^{+ve}$ cells. However, inspection of the RT PCR data reveals that HDAC9 is specifically expressed in TEL-AML1 positive and negative pre-B cell acute lymphoblastic leukaemia, and B cell lymphoma cell lines and patient samples. HDAC9 is not expressed in various acute myeloid leukaemia cell lines, with the exception of acute monocytic leukaemia, possibly reflecting a common progenitor for B cell and monocytic lineages. HDAC9 is also found at lower levels in the erythroleukemia cell line, HEL. The cell line which overexpress HDAC9 also express the ΔExon7 and ΔExon12 isoforms at higher levels and in one the of CLL patient samples which have been stimulated with SAC/IL2, there is a clear change in the relative expression of full length and ΔExon12 isoforms. There is evidence that the addition of HDAC inhibitors can alter the cellular distribution of HDACs presumably through interfering with protein-protein interactions as well blocking the catalytic site and this potential of HDAC9 in recruiting and modifying of other proteins, as well histone deacetylation. Taking this into consideration, the ΔExon7 may prove to be very important in the pathogenesis of some leukaemias.

In this context, there are a number of methods known in the art for analysing samples from individuals to determine the presence of HDAC9 nucleic acid or polypeptide. The assays may determine the presence or amount of HDAC9 nucleic acid or polypeptide in a sample from a patient, and whether the nucleic acid or polypeptide is full length or has a HDAC9 biological activity. Examples of biological samples include blood, plasma, serum, tissue samples, tumour samples, saliva and urine. The purpose of such analysis may be used for diagnosis or prognosis, to assist a physician in determining the severity or likely course of the condition and/or to optimise treatment of it.

Exemplary approaches for detecting HDAC9 nucleic acid or polypeptides include:

(a) determining the presence or amount of HDAC9 polypeptide in a sample from a patient, by measuring an activity of the HDAC9 polypeptide or its presence in a binding assay; or, (b) determining the presence of HDAC9 nucleic acid using a probe capable of hybridising to the HDAC9 nucleic acid;

(c) using PCR involving one or more primers based on a HDAC9 nucleic acid sequence to determine whether the HDAC9 transcript is present in a sample from a patient.

In one embodiment, the method comprises the steps of:

(a) contacting a sample obtained from the patient with a solid support having immobilised thereon binding agent having binding sites specific for HDAC9 polypeptide or HDAC9 nucleic acid;

(b) contacting the solid support with a labelled developing agent capable of binding to unoccupied binding sites, bound HDAC9 polypeptide or nucleic acid or occupied binding sites; and, (c) detecting the label of the developing agent specifically binding in step (b) to obtain a value representative of the presence or amount of the HDAC9 polypeptide or nucleic acid in the sample.

The binding agent preferably is a specific binding agent and has one or more binding sites capable of specifically binding to HDAC9 or nucleic acid in preference to other molecules. Conveniently, the binding agent is immobilised on solid support, e.g. at a defined location, to make it easy to manipulate during the assay.

Examples of specific binding pairs are antigens and antibodies, molecules and receptors and complementary nucleotide sequences. The skilled person will be able to think of many other examples and they do not need to be listed here. Further, the term "specific binding pair" is also applicable where either or both of the specific binding member and the binding partner comprise a part of a larger molecule. In embodiments in which the specific binding pair are nucleic acid sequences, they will be of a length to hybridise to each other under the conditions of the assay, preferably greater than 10 nucleotides long, more preferably greater than 15 or 20 nucleotides long.

There are various methods for determining the presence or absence in a test sample of a particular nucleic acid sequence, such as the sequence shown in FIG. 2.

Exemplary tests include nucleotide sequencing, hybridisation using nucleic acid immobilized on chips, molecular phenotype tests, protein truncation tests (PTT), single-strand conformation polymorphism (SSCP) tests, mismatch cleavage detection and denaturing gradient gel electrophoresis (DGGE). These techniques and their advantages and disadvantages are reviewed in Nature Biotechnology, 15:422-426, 1997.

Pharmaceutical Compositions

The present invention disclose the use of HDAC9 or inhibitors thereof for formulation in pharmaceutical compositions, and especially compositions for the treatment of cancer, and more especially leukaemias such as TEL-AML1 positive and negative pre-B cell acute lymphoblastic leukaemia, and B cell lymphoma. These compositions may comprise, in addition to one of the above substances, a pharmaceutically acceptable excipient, carrier, buffer, stabiliser or other materials well known to those skilled in the art.

Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub.

Lippincott, Williams & Wilkins. A composition may be administered alone or in combination with other treatments, either simultaneously or sequentially, dependent upon the condition to be treated.

EXPERIMENTAL

Cloning of HDAC9

Figure 1:
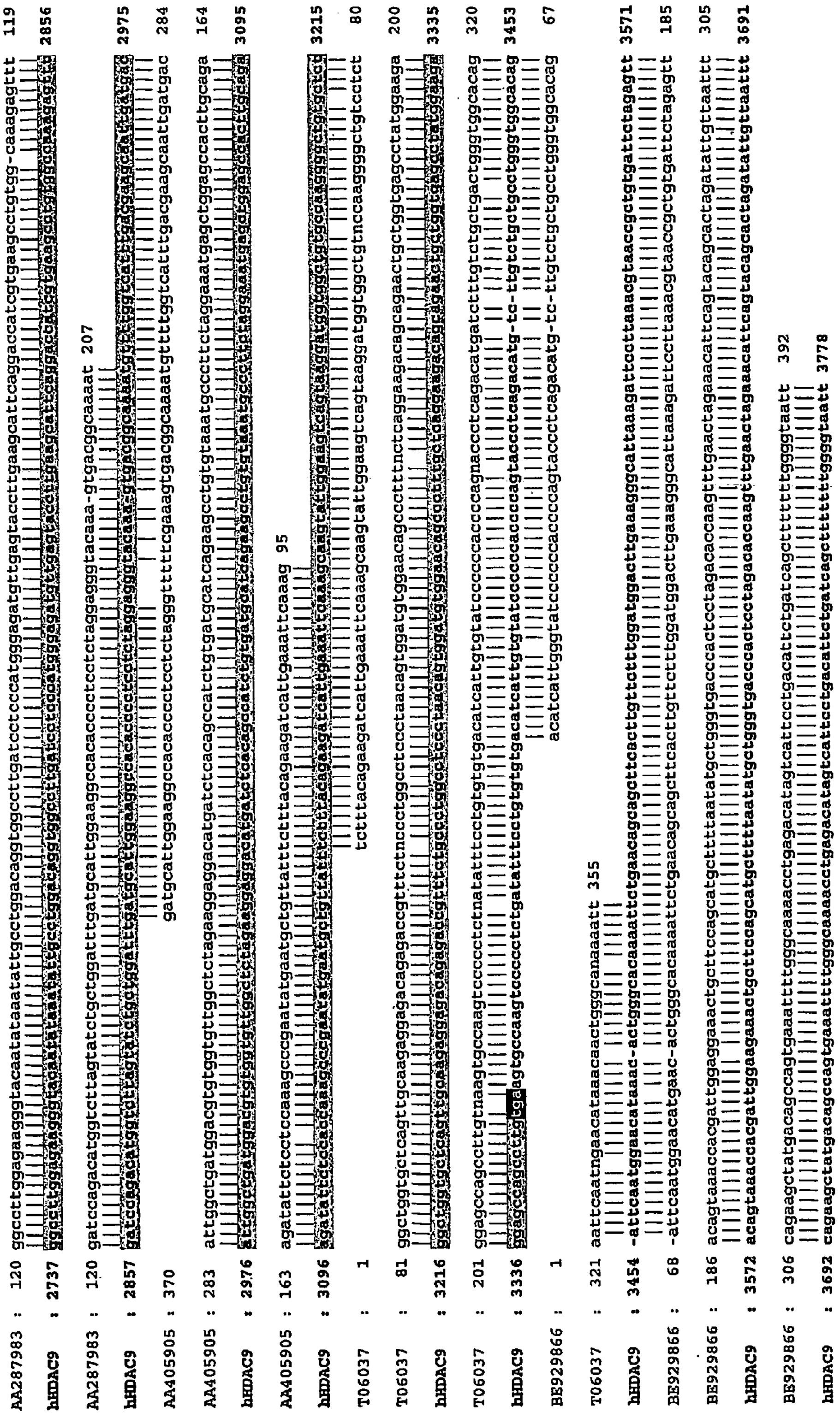
FIG. 1. Schematic representation of the rational behind the cloning of the 3' end HDAC9. EST accession nos. (AA287983—SEQ ID NO: 6; AA405905—SEQ ID NO: 7; T06037—SEQ ID NO: 8; BE929866—SEQ ID NO: 9) are indicated on the left with position numbers on the right. HDAC9 sequence (SEQ ID NO: 1 at indicated nucleotides) is shown in bold and highlighted in grey. Sequence identity is indicated by vertical lines. The EST database at the NCBI was screened with EST sequences corresponding to HDAC9 cDNA found through homology to HDAC5. A number of overlapping clones were obtained which enabled the cloning of HDAC9 through the design of specific primers.
Figure 3:
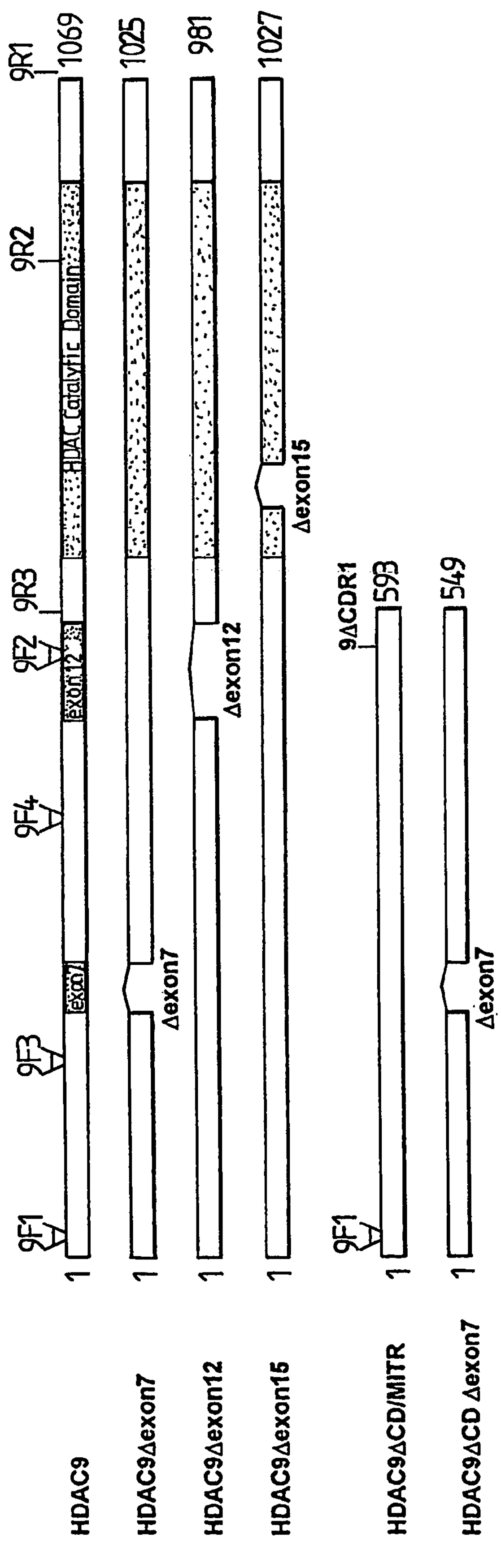
FIG. 3. Schematic representation of HDAC9 isoforms. The length of the various HDAC9 isoforms together with the primers used in cloning and RT-PCR analysis.
Figure 4A:
FIG. 4. Analysis of HDAC9 sequence.
Figures 4B, 4C:
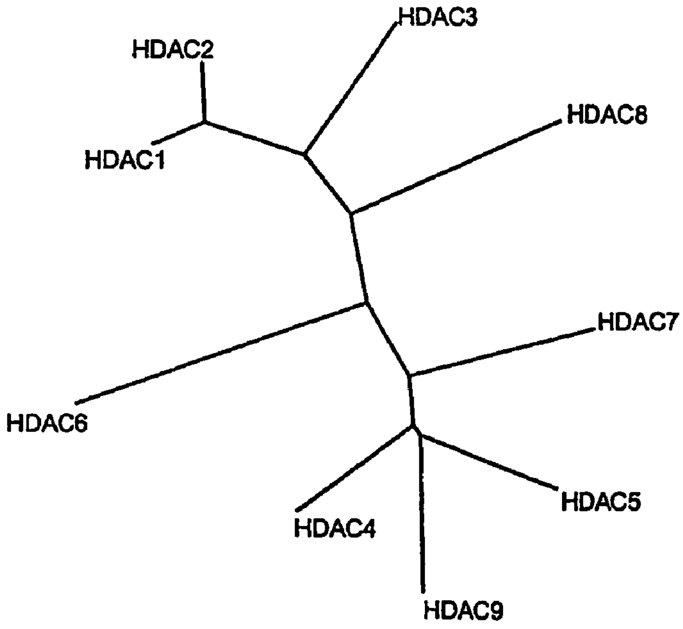

The National Institute for Biotechnology Information (NCBI) high throughput genomic sequence database (htgs) was searched with the amino acid sequences corresponding to the deacetylase domain of HDAC5 in an effort to identify novel histone deacetylase genes. Several DNA sequences encoding peptides with significant homology to HDAC5 were found on a human BAC clone RP11-8115 (accession no. AC016186) which contains 70 unordered contigs and maps to chromosome 18. When the Genbank nucleotide database was searched with a composite of the novel sequences showing homology to HDAC5, it aligned with BAC clone CTB-13P7 (accession no. AC002088) which mapped to chromosome 7p15-p21 (Table 1), indicating the presence of a pseudogene or incorrect entry into the htgs database. A search of the literature revealed that 7p15-p21 had already been identified as containing a potential HDAC open reading frame and that a gene encoding a protein called HDRP/MITR which shares 50% identity with the N-terminus of HDACs 4 and 5, had been cloned and also mapped to this genomic region. Since a search of the expressed sequence tag database (dbEST) revealed that cDNA corresponding to a partial HDAC domain had been isolated from germinal centre B cells (accession no. AA287983), several hematopoietic cell lines were analysed by reverse transcription (RT)-PCR with oligonucleotides corresponding to the HDAC domain and HDRP/MITR. It was found that not only was it possible to amplify bands from the HDAC domain itself but also from the cDNA of HDRP/MITR through to the HDAC domain and this resulted in the generation of around 2700 bp of sequence. 3' RACE failed to yield the remaining sequence so an attempt was made to try to find overlapping ESTs in order to 'walk' along the cDNA (FIG. 1) and confirm any matching sequence against the genomic clones. During this investigation, it became apparent that the sequence corresponding to the final 5 exons of HDAC9 (accession no. RP5-1194E15 and GS1-465N13) had been submitted in the antisense direction in relation to the rest of the gene (see Table 1). As these clones accounted for almost 160 kb of DNA (out of a total of 500 kb for the entire gene), search algorithms had not previously identified homology between the EST and genomic sequences. Clones spanning the HDAC9 gene are listed in Table 2. When the database searches were repeated with the last two genomic clones in the correct orientation, an alignment was obtained, which showed significant homology with the sequence for HDACs 4 and 5. This information permitted the cloning of the entire open reading frame of HDAC9 (FIG. 2) from Marathon-Ready Human Brain cDNA (Clontech) using the sense primer 9F1 5'-ATGCACAGTATGATCAGCTCA-3' (SEQ ID NO: 63) and the antisense primer 9R1 5'-GTCACACACAGGAAATATCAG-3' (SEQ ID NO: 64). HDAC9ΔCD/HDRP/MITR was cloned from Marathon-Ready Human Brain cDNA (Clontech) using the sense primer 9F1 and the antisense primer 9Δ CDR1 5'-TCAGATAATGACTTTAATACAAAT-3' (SEQ ID NO: 65; see FIG. 2 for the cDNA sequence and translation). HDAC9ΔExon7 and HDAC9ΔExon12 were cloned from the acute monocytic leukaemia cell line MONO-MAC-6 using the sense primer 9F1 and the antisense primer 9R3 5'-TCTCTAATCCATCCATGCCAA-3' (SEQ ID NO: 66). HDAC9ΔExon15 was cloned from the acute Pre-B ALL cell line REH using the sense primer 9F2 5'-AGGCTGCTTTTATGCAACAG-3' (SEQ ID NO: 67) and the antisense primer 9R2 5'-CTGAATGCTTCAAGGTACTCA-3' (SEQ ID NO: 68). See FIG. 3 for a schematic detailing the positions of the above primers. PCR products were cloned into pCRII (Invitrogen) and sequenced using BigDye (Perkin Elmer).

Analysis of HDAC9 Sequence

The full-length product of the HDAC9 gene comprises 1069 amino acids as shown in FIGS. 2 (see FIG. 3 for schematic), and is encoded by exons 2-26 (exon 1 is untranslated). The 26 exons, which form the HDAC9 cDNA, span 500 kb of genomic sequence on chromosome 7p15-p21. HDAC9ΔCD, also referred to as HDRP/MITR is 593 amino acids in length and contains 16 residues of unique sequence encoded by a region of exon 12 which is 3' to the splice donor site used to generate the HDAC9 ORF. There are several exon deletions which may occur that preserve the open reading frame of HDAC9 (Table 2) and two have been identified and cloned. HDAC9Δexon7 is 1025 amino acids long and contains an Ala to Glu substitution at position 222 as the result of the deletion of exon 7. This isoform lacks two serines (S223 and S253) which when phosphorylated have been implicated in 14-3-3 protein dependent shuttling of HDAC4 and 5 from the nucleus to the cytoplasm, and also a tripartite nuclear localization signal. HDAC9Δexon12 is 981 amino acids long and lacks exon 12 sequences encoding a leucine zipper motif that may mediate interactions of HDAC9 with other proteins.

An isoform, which possesses neither exon 7 nor exon 12, has also been cloned. HDAC9Δexon15 is 1027 amino acids long and lacks a region within the catalytic domain adjacent to the active site. This isoform does not naturally conserve the ORF of HDAC9 and appears to have undergone RNA editing as shown below.

```
                    exon14          exon16
HDAC9        5'-aaa tgt gag -exon15- gt gat gac-3'

HDAC9Δexon15 5'-aaa tgt                 gac gac-3'
                 K   C                   D   D
```

Additionally, exon 4 may be deleted, which introduces an in-frame stop codon and results in a truncated protein of 95 amino acids. Exon 4 may also be alternatively spliced at either end as indicated in Table 2.

HDAC9 Possesses Histone Deacetylase Activity and Represses Basal Transcription

In order to determine whether HDAC9 possesses histone deacetylase activity, an in-vitro assay was performed using anti-FLAG immunoprecipitated HDAC9. As shown in FIG. 5A, HDAC9 contains about 25% activity of HDAC1 and 50% activity of HDACs 4 and 5. Higher activities of HDAC9 have been detected towards peptide substrates derived from histone H3 than from histone H4 (FIGS. 7A and B).

It has been previously established that HDACs repress transcription when tethered to DNA as Gal4 fusion proteins. This effect is also observed with HDAC9, HDAC9ΔCD and HDAC9CD alone (FIG. 5B). A GAL4$^{uas}$x5-TK-Luciferase reporter gene was transiently transfected into 293T cells together with the expression vectors for the indicated GAL4 fusion proteins. The repressive effects of various GAL4 DBD-HDAC9 fusions were partially relieved by the addition of the HDAC inhibitor Trichostatin A, including that of HDAC9ΔCD. Although HDAC9ΔCD lacks an HDAC domain it has been shown to bind other HDACs directly and via co-repressors, and this may be reflected in its ability to repress in a TSA sensitive manner. These results indicate that HDAC9 is able to use Histone H4 as a substrate and functions, at least in part, as a component of the repression machinery of the cell.

Expression Patterns of HDAC9 in Normal Human Tissue and Cancer Cells

Figure 8A:
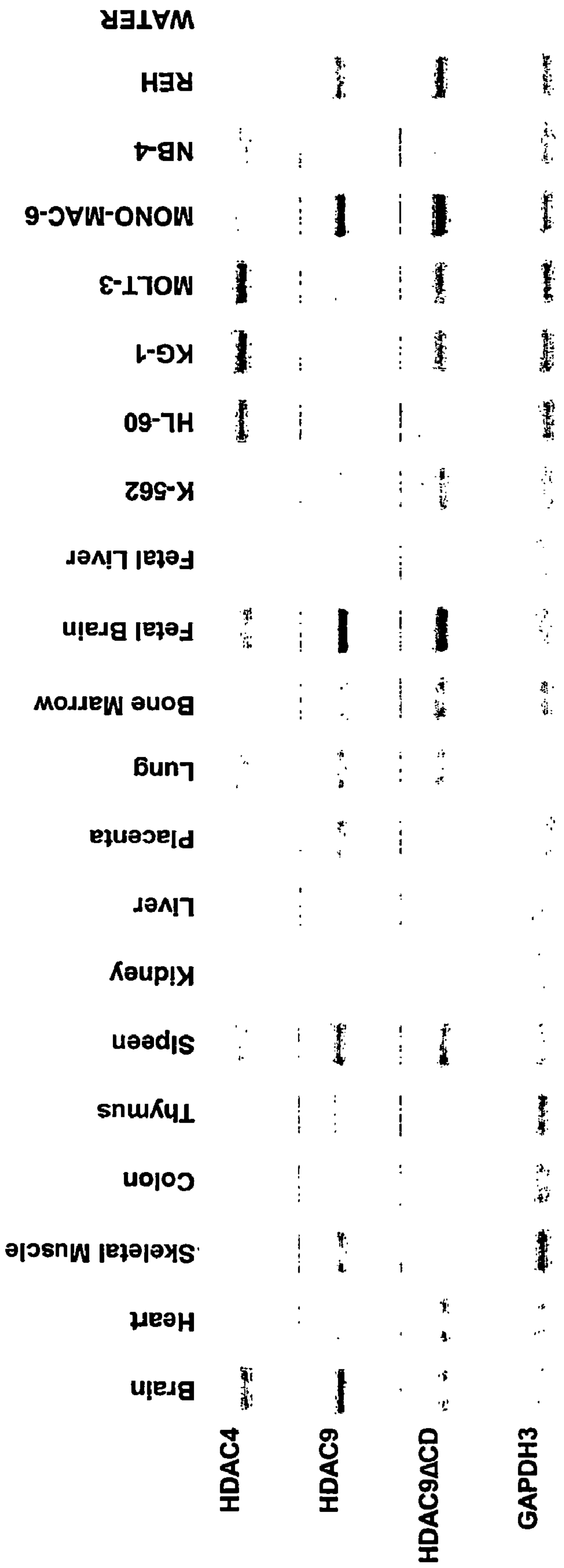
Figure 8B:
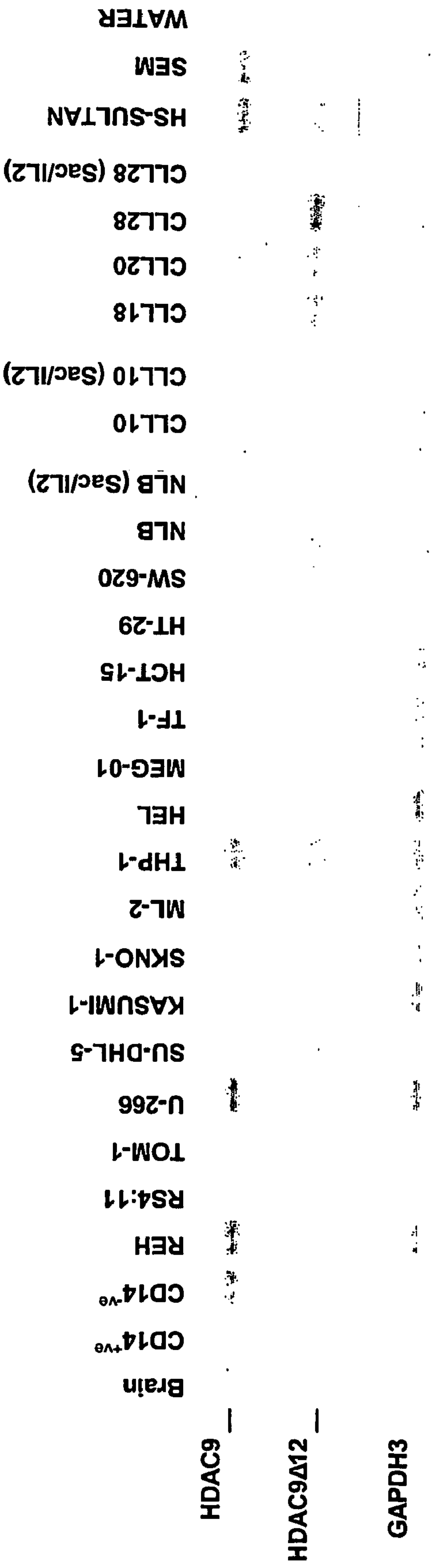
Figure 8C:
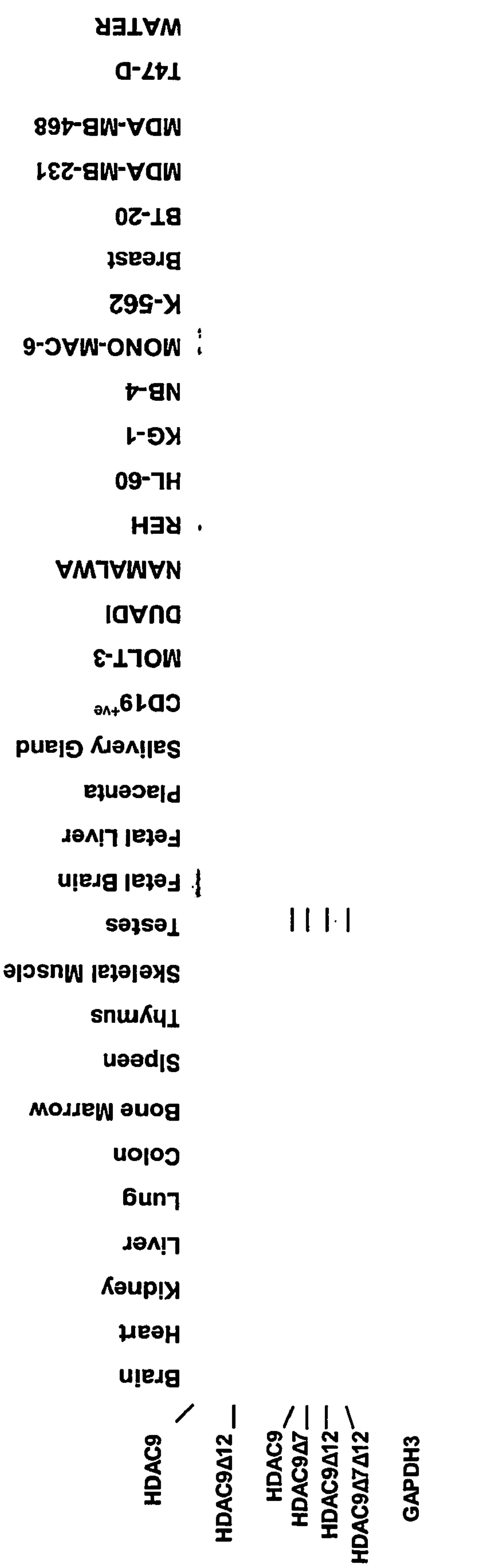

Under normal circumstances, the expression of HDAC9 isoforms which contain the catalytic domain appears to be tightly regulated, with the protein only found at high levels in adult and foetal brain, and to a lesser extent skeletal muscle, testes, bone marrow, thymus, spleen, CD14$^{+ve}$, and CD19$^{+ve}$ cells (FIG. 8). However, inspection of RT-PCR data reveals that HDAC9 is specifically expressed in TEL-AML1 positive and negative pre-B cell acute lymphoblastic leukaemia samples, and B cell lymphoma cell lines and patient samples (FIGS. 8A and B). HDAC9 is not expressed in various acute myeloid leukaemia cell lines, with the exception of acute monocytic leukaemia, possibly reflecting a common progenitor for B cell and monocytic lineages. HDAC9 is also found at lower levels in the erythroleukemia cell line, HEL. The leukaemic cell lines, which over-express HDAC9, also over-express the isoforms lacking exon7 and exon12 relative to normal levels (see FIGS. 8B and C). In one the CLL patient sample that has been stimulated with SAC/IL2, there is a clear change in the relative expression of full length and ΔExon12 isoforms (FIG. 8C). There is evidence that the addition of HDAC inhibitors can alter the cellular distribution of HDACs presumably through interfering with protein-protein interactions as well blocking the catalytic site with respect to HDAC9, such findings should be considered in the context of various isoforms and their function. HDAC9 isoforms lacking functional domains encoded by exons 7 or 12 may prove to be an important factor in the pathogenesis of some hematalogical malignancies.

In-Vitro and In-Vivo Interactions of HDAC9

Given the expression patterns of the HDAC9 gene in the normal and malignant cells deriving from the B cell lineage, we examined whether its products could interact with any of the proteins whose function has been implicated in B-cell malignancies (FIG. 9). As expected, HDAC9 was found to interact with Diffuse Large Cell Lymphoma and pre-B cell acute lymphoblastic leukaemia associated transcriptional repressors BCL-6 and TEL, respectively. HDAC9 also interacted with PLZF, HDAC 4 and to a lesser degree class I HDACs 1 and 3. In addition HDAC9 was found to interact with the nuclear receptor co-repressors mSin3A and B and N-CoR, whose activities have been implicated in the mechanism underlying pathogeneses of several human cancers.

FIG. 10 shows the cellular localization of various HDAC9 isoforms when visualized with anti-FLAG antibody and an antibody to the N-terminal epitope present in all of the HDAC9 isoforms. Note that HDAC9Δexon7 is completely excluded from the nucleus. To further analyse the interactions of HDAC9 isoforms in vivo, we performed the co-immunofluorescence assays (FIG. 11-13). When HDAC9 was co-expressed with BCL-6, PLZF and N-CoR, it was shown to colocalize with them in-vivo and to influence their wild type localization towards a pattern seen for a given HDAC9 isoform. These data indicated those in vitro interactions between the HDAC9 and a number of other proteins (see above and FIG. 9) can also be observed in vivo. For example, when HDAC9Δexon7 was co-expressed with a given interaction partner there was a dramatic change in its cellular localization, with HDAC9Δexon7 recruiting it to the cytoplasm (see FIG. 10).

The references mentioned herein are all expressly incorporated by reference.

TABLE 1

Human HDAC9 exon/intron splice junctions

| Exon | Frame | Size | 5' Splice Donor | Intron | Size | 3' Splice Acceptor |
|---|---|---|---|---|---|---|
| 1 | — | 109 | TCTAAGCCAG**gt**ttaattggtt | 1 | 407 | gtttttcctc**ag**ATGGGGTGGC |
| 2 | 1 | 63 | ATCAGCTCAG**gt**aagatcctct | 2 | 88956 | ctggttcttt**ag**TGGATGTGAA |

TABLE 1-continued

| | | | | | | |
|---|---|---|---|---|---|---|
| 3 | 2 | 242 | GCATATCAAGgtagcaaatgct | 3a | 4812 | tcttctcgcaagTTGCAACAGG |
| 3 | 2 | | | 3b | | aagttgcaacagGAACTTCTAG |
| 4 | 1 | 142 | GGACGAGAAAgtaagaggcacc | 4c | | |
| 4 | 1 | | AGGCACCAGGgtaaacgatgga | 4d | 1014 | tgtgtatttcagGGGCAGTGGC |
| 5 | 2 | 127 | TCTGGTACACgtatgttcagtg | 5 | 2265 | tgtcttttctagGGCTGCCCAC |
| 6 | 3 | 122 | CGAAAAACTGgtaagttggttt | 6 | 35320 | ctcaatccccagCCTCTGAGCC |
| 7 | 2 | 132 | GAGGTGACAGgtaattgaggac | 7 | 5145 | aatatttttcagAATCCTCAGT |
| 8 | 2 | 116 | TCATGCCGAGgtaagaccctta | 8 | 9928 | tttttttaacagCAAATGGTTT |
| 9 | 1 | 123 | CCAGCTCAATgtaagtcattgc | 9 | 2991 | ttctcaacacagGCTTCGAATT |
| 10 | 1 | 214 | CTTGTAGCTGgtaattcattat | 10 | 467 | tttttttttcagGTGGAGTTCC |
| 11 | 2 | 218 | CATGAACAAAgtaagcctccaa | 11 | 17529 | actctcttctagCTGCTTTCGA |
| 12 | 1 | 264 | TATGCAACAGgtaataggcaaa | 12 | 58741 | tcttggcaacagCCTTTCCTGG |
| 13 | 1 | 178 | TCTGCAACTGgtaggaatccct | 13 | 21243 | cttgtcttaaagGAATTGCCTA |
| 14 | 2 | 134 | TAAATGTGAGgtaatccagaat | 14 | 13018 | attttcttgcagCGAATTCAAG |
| 15 | 1 | 121 | ATACTCCTAGgtctgtacgggc | 15 | 4828 | cttactgtatagGTGATGACTC |
| 16 | 2 | 50 | TGGACTTGGGgtaagtacaagt | 16 | 26189 | ctgtttgctcagGTGGACAGTG |
| 17 | 1 | 108 | AGAGCTGAAGgtgaggtccggg | 17 | 35708 | ttgttttcacagAATGGGTTTG |
| 18 | 1 | 56 | CCACAGCCATgtaagtaccagg | 18 | 244 | tctattccgcagGGGGTTCTGC |
| 19 | 3 | 88 | TGTAGATCTGgtatgtattcct | 19 | 5921 | atttccctgtagGATGTTCACC |
| 20 | 1 | 120 | CCCAAATGAGgttcggtttatt | 20 | 313 | ttctcttcccagGTTGGAACAG |
| 21 | 1 | 98 | AAGCATTCAGgttggtacttct | 21 | 38480 | tttactgtgcagGACCATCGTG |
| 22 | 3 | 119 | ACGGCAAAATgtaagtacctct | 22 | 61212 | gtattatggtagGTTTTGGTCA |
| 23 | 2 | 134 | AGGAAATGAGgtaaaaaagtaa | 23 | 18203 | ctattcttgcagCTGGAGCCAC |
| 24 | 1 | 85 | GAAATTCAAAgtatgtctttaa | 24 | 21575 | tgtttttcctagGCAAGTATTG |
| 25 | 2 | 148 | AAGACAGCAGgtatgaatccaa | 25 | 20069 | ttatttttacagAACTGCTGGT |
| 26 | 3 | 40 | | | | |

Consensus splice donor (SEQ ID NOs: 10, 12, 14, 17, 18, 20, 22, 24, 26, 28, 30, 32, 34, 36, 38, 40, 42, 44, 46, 48, 50, 52, 54, 56, 58, and 60, from top to bottom) and acceptor (SEQ ID NOs: 11, 13, 15, 16, 19, 21, 23, 25, 27, 29, 31, 33, 35, 37, 39, 41, 43, 45, 47, 49, 51, 53, 55, 57, 59, and 61, from top to bottom) sequences between exons (uppercase) and introns (lowercase) are underlined. Exons highlighted in ■ have the potential to be spliced out in-frame. Δ exon 7 and 12 cDNAs have already been detected. The suffixes a, b, c and d refer to the alternative splice sites at ether end of exon 4. i.e. (SEQ ID NO: 62)

```
                     a      b
cacactctcatgtctttctcttctcgcaagTTGCAACagGAACTTCTAGCCATAAAACAGCAACAAGA

ACTCCTAGAAAAGGAGCAGAAACTGGAGCAGCAGAGGCAAGAACAGGAAGTAG

AGAGGCATCGCAGAGAACAGCAGCTTCCTCCTCTCAGAGGCAAAGATAGAGGAC

GAGAAA

gtAAGAGGCACCAGGgtaaacgatggactctctttcctcatcgttagctgatcattatt
c      d
```

Areas shown in italics at either end of Exon4 refer to alternatively splices regions of the exon that have been detected.

TABLE 2

Genomic organization of HDAC9 and its MITR isoform

| Exon | Clone | Accession # | Location on BAC | Relative position |
|---|---|---|---|---|
| MITR/ HDAC9 5' | | | | |
| 1 | CTA-317M2 | AC002433 | 43921-44029 | 1-110 |
| 2 | " | " | 44434-44499 | 517-580 |
| 3 | " | " | 133456-133699 | 89536-89779 |
| 4 | " | " | 138520-138661 | 94600-94742 |
| 5 | " | " | 139691-139817 | 95771-95898 |
| 6 | CTB-180O1 | AC002124 | 2364-2485 | 98163-98283 |
| 7 | " | " | 37086-37937 | 133605-133737 |
| 8 | " | " | 43083-43198 | 138882-138998 |
| 9 | " | " | 53127-53249 | 148926-149049 |
| 10 | " | " | 56241-56454 | 152040-152254 |

TABLE 2-continued

Genomic organization of HDAC9 and its MITR isoform

| Exon | Clone | Accession # | Location on BAC | Relative position |
|---|---|---|---|---|
| 11 | " | " | 56922-57139 | 152721-152939 |
| 12a | " | " | 74669-77298 | 170468-173098 |
| HDAC9 3' | | | | |
| 12b | CTB-180O1 | AC002124 | 74669-74932 | 170468-170732 |
| 13 | CTB-13P7 | AC002088 | 35119-35296 | 231839-232017 |
| 14 | " | " | 56544-56677 | 253260-253394 |
| 15 | " | " | 69696-69816 | 266412-266533 |
| 16 | " | " | 74645-74694 | 271361-271411 |
| 17 | CTA-264L19 | AC002410 | 15451-15558 | 297600-297708 |
| 18 | " | " | 51267-51322 | 333416-333472 |
| 19 | " | " | 51567-51654 | 333716-333801 |
| 20 | " | " | 57573-57692 | 339722-339842 |
| 21 | " | " | 58006-58103 | 340155-340253 |

TABLE 2-continued

Genomic organization of HDAC9 and its MITR isoform

| Exon | Clone | Accession # | Location on BAC | Relative position |
|---|---|---|---|---|
| 22 | RP5-1194E15 | AC004994 | 79771-79643 | 378733-378852 |
| 23 | " | " | 18434-18301 | 440064-440198 |
| 24 | GS1-465N13 | AC004744 | 85480-85390 | 458401-458486 |
| 25 | " | " | 63816-63669 | 480061-480209 |
| 26 | " | " | 43602-43430 | 500278-500449 |

The invention claimed is:

1. An isolated polypeptide possessing histone deacetylase activity, said polypeptide having at least 95% amino acid sequence identity over the full length of SEQ ID NO: 2.

2. The isolated polypeptide of claim 1, wherein the polypeptide has the amino acid sequence of SEQ ID NO: 2.

3. An isolated polypeptide having histone deacetylase activity, wherein the polypeptide is encoded by a nucleic acid which comprises a sequence encoding amino acids 1009 to 1069 of the polypeptide of SEQ ID NO: 2, or a complement thereof, said nucleic acid hybridizing to SEQ NO: 1 under stringent conditions, wherein said stringent conditions comprise 50% (v/v) formamide, 760 mM sodium chloride, 75 mM sodium citrate, 0.1% bovine serum albumin, 0.1% Ficoll, and 0.1% polyvinylpyrrolidone, in 50 mM sodium phosphate buffer at pH 6.5 at 42° C.

4. The isolated polypeptide of claim 1 which is joined to a coupling partner.

5. The isolated polypeptide of claim 4, wherein the coupling partner is selected from the group consisting of an effector molecule, a label, a drug and a toxin.

6. A method of producing a histone deacetylase polypeptide according to claim 1 comprising culturing host cells comprising at least one nucleic acid molecule that encodes said histone deacetylase polypeptide, such that said histone deacetylase polypeptide is produced in said cell and isolating the polypeptide thus produced.

7. A composition comprising an isolated polypeptide possessing histone deactylase activity, as claimed in claim 1, and a pharmaceutically acceptable excipient, carrier, buffer or stabilizer.

* * * * *

SEQUENCE LISTING

```
<160> NUMBER OF SEQ ID NOS: 68

<210> SEQ ID NO 1
<211> LENGTH: 3955
<212> TYPE: DNA
<213> ORGANISM: Homo sapiens
<220> FEATURE:
<221> NAME/KEY: CDS
<222> LOCATION: (151)..(3360)

<400> SEQUENCE: 1

ggggaagaga ggcacagaca cagataggag aagggcaccg gctggagcca cttgcaggac      60

tgagggtttt tgcaacaaaa ccctagcagc ctgaagaact ctaagccaga tggggtggct     120

ggacgagagc agctcttggc tcagcaaaga atg cac agt atg atc agc tca gtg      174
                                 Met His Ser Met Ile Ser Ser Val
                                   1               5

gat gtg aag tca gaa gtt cct gtg ggc ctg gag ccc atc tca cct tta       222
Asp Val Lys Ser Glu Val Pro Val Gly Leu Glu Pro Ile Ser Pro Leu
     10                  15                  20

gac cta agg aca gac ctc agg atg atg atg ccc gtg gtg gac cct gtt       270
Asp Leu Arg Thr Asp Leu Arg Met Met Met Pro Val Val Asp Pro Val
 25                  30                  35                  40

gtc cgt gag aag caa ttg cag cag gaa tta ctt ctt atc cag cag cag       318
Val Arg Glu Lys Gln Leu Gln Gln Glu Leu Leu Leu Ile Gln Gln Gln
                 45                  50                  55

caa caa atc cag aag cag ctt ctg ata gca gag ttt cag aaa cag cat       366
Gln Gln Ile Gln Lys Gln Leu Leu Ile Ala Glu Phe Gln Lys Gln His
             60                  65                  70

gag aac ttg aca cgg cag cac cag gct cag ctt cag gag cat atc aag       414
Glu Asn Leu Thr Arg Gln His Gln Ala Gln Leu Gln Glu His Ile Lys
         75                  80                  85

ttg caa cag gaa ctt cta gcc ata aaa cag caa caa gaa ctc cta gaa       462
Leu Gln Gln Glu Leu Leu Ala Ile Lys Gln Gln Gln Glu Leu Leu Glu
     90                  95                 100

aag gag cag aaa ctg gag cag cag agg caa gaa cag gaa gta gag agg       510
Lys Glu Gln Lys Leu Glu Gln Gln Arg Gln Glu Gln Glu Val Glu Arg
105                 110                 115                 120

cat cgc aga gaa cag cag ctt cct cct ctc aga ggc aaa gat aga gga       558
His Arg Arg Glu Gln Gln Leu Pro Pro Leu Arg Gly Lys Asp Arg Gly
                125                 130                 135

cga gaa agg gca gtg gca agt aca gaa gta aag cag aag ctt caa gag       606
Arg Glu Arg Ala Val Ala Ser Thr Glu Val Lys Gln Lys Leu Gln Glu
            140                 145                 150

ttc cta ctg agt aaa tca gca acg aaa gac act cca act aat gga aaa       654
```

-continued

```
Phe Leu Leu Ser Lys Ser Ala Thr Lys Asp Thr Pro Thr Asn Gly Lys
        155                 160                 165

aat cat tcc gtg agc cgc cat ccc aag ctc tgg tac acg gct gcc cac      702
Asn His Ser Val Ser Arg His Pro Lys Leu Trp Tyr Thr Ala Ala His
    170                 175                 180

cac aca tca ttg gat caa agc tct cca ccc ctt agt gga aca tct cca      750
His Thr Ser Leu Asp Gln Ser Ser Pro Pro Leu Ser Gly Thr Ser Pro
185                 190                 195                 200

tcc tac aag tac aca tta cca gga gca caa gat gca aag gat gat ttc      798
Ser Tyr Lys Tyr Thr Leu Pro Gly Ala Gln Asp Ala Lys Asp Asp Phe
                205                 210                 215

ccc ctt cga aaa act gcc tct gag ccc aac ttg aag gtg cgg tcc agg      846
Pro Leu Arg Lys Thr Ala Ser Glu Pro Asn Leu Lys Val Arg Ser Arg
            220                 225                 230

tta aaa cag aaa gtg gca gag agg aga agc agc ccc tta ctc agg cgg      894
Leu Lys Gln Lys Val Ala Glu Arg Arg Ser Ser Pro Leu Leu Arg Arg
        235                 240                 245

aag gat gga aat gtt gtc act tca ttc aag aag cga atg ttt gag gtg      942
Lys Asp Gly Asn Val Val Thr Ser Phe Lys Lys Arg Met Phe Glu Val
    250                 255                 260

aca gaa tcc tca gtc agt agc agt tct cca ggc tct ggt ccc agt tca      990
Thr Glu Ser Ser Val Ser Ser Ser Ser Pro Gly Ser Gly Pro Ser Ser
265                 270                 275                 280

cca aac aat ggg cca act gga agt gtt act gaa aat gag act tcg gtt     1038
Pro Asn Asn Gly Pro Thr Gly Ser Val Thr Glu Asn Glu Thr Ser Val
                285                 290                 295

ttg ccc cct acc cct cat gcc gag caa atg gtt tca cag caa cgc att     1086
Leu Pro Pro Thr Pro His Ala Glu Gln Met Val Ser Gln Gln Arg Ile
            300                 305                 310

cta att cat gaa gat tcc atg aac ctg cta agt ctt tat acc tct cct     1134
Leu Ile His Glu Asp Ser Met Asn Leu Leu Ser Leu Tyr Thr Ser Pro
        315                 320                 325

tct ttg ccc aac att acc ttg ggg ctt ccc gca gtg cca tcc cag ctc     1182
Ser Leu Pro Asn Ile Thr Leu Gly Leu Pro Ala Val Pro Ser Gln Leu
    330                 335                 340

aat gct tcg aat tca ctc aaa gaa aag cag aag tgt gag acg cag acg     1230
Asn Ala Ser Asn Ser Leu Lys Glu Lys Gln Lys Cys Glu Thr Gln Thr
345                 350                 355                 360

ctt agg caa ggt gtt cct ctg cct ggg cag tat gga ggc agc atc ccg     1278
Leu Arg Gln Gly Val Pro Leu Pro Gly Gln Tyr Gly Gly Ser Ile Pro
                365                 370                 375

gca tct tcc agc cac cct cat gtt act tta gag gga aag cca ccc aac     1326
Ala Ser Ser Ser His Pro His Val Thr Leu Glu Gly Lys Pro Pro Asn
            380                 385                 390

agc agc cac cag gct ctc ctg cag cat tta tta ttg aaa gaa caa atg     1374
Ser Ser His Gln Ala Leu Leu Gln His Leu Leu Leu Lys Glu Gln Met
        395                 400                 405

cga cag caa aag ctt ctc gta gct ggt gga gtt ccc tta cat cct cag     1422
Arg Gln Gln Lys Leu Leu Val Ala Gly Gly Val Pro Leu His Pro Gln
    410                 415                 420

tct ccc ttg gca aca aaa gag aga att tca cct ggc att aga ggt acc     1470
Ser Pro Leu Ala Thr Lys Glu Arg Ile Ser Pro Gly Ile Arg Gly Thr
425                 430                 435                 440

cac aaa ttg ccc cgt cac aga ccc ctg aac cga acc cag tct gca cct     1518
His Lys Leu Pro Arg His Arg Pro Leu Asn Arg Thr Gln Ser Ala Pro
                445                 450                 455

ttg cct cag agc acg ttg gct cag ctg gtc att caa cag caa cac cag     1566
Leu Pro Gln Ser Thr Leu Ala Gln Leu Val Ile Gln Gln Gln His Gln
            460                 465                 470
```

-continued

```
caa ttc ttg gag aag cag aag caa tac cag cag cag atc cac atg aac      1614
Gln Phe Leu Glu Lys Gln Lys Gln Tyr Gln Gln Gln Ile His Met Asn
        475                 480                 485

aaa ctg ctt tcg aaa tct att gaa caa ctg aag caa cca ggc agt cac      1662
Lys Leu Leu Ser Lys Ser Ile Glu Gln Leu Lys Gln Pro Gly Ser His
    490                 495                 500

ctt gag gaa gca gag gaa gag ctt cag ggg gac cag gcg atg cag gaa      1710
Leu Glu Glu Ala Glu Glu Glu Leu Gln Gly Asp Gln Ala Met Gln Glu
505                 510                 515                 520

gac aga gcg ccc tct agt ggc aac agc act agg agc gac agc agt gct      1758
Asp Arg Ala Pro Ser Ser Gly Asn Ser Thr Arg Ser Asp Ser Ser Ala
                525                 530                 535

tgt gtg gat gac aca ctg gga caa gtt ggg gct gtg aag gtc aag gag      1806
Cys Val Asp Asp Thr Leu Gly Gln Val Gly Ala Val Lys Val Lys Glu
            540                 545                 550

gaa cca gtg gac agt gat gaa gat gct cag atc cag gaa atg gaa tct      1854
Glu Pro Val Asp Ser Asp Glu Asp Ala Gln Ile Gln Glu Met Glu Ser
        555                 560                 565

ggg gag cag gct gct ttt atg caa cag cct ttc ctg gaa ccc acg cac      1902
Gly Glu Gln Ala Ala Phe Met Gln Gln Pro Phe Leu Glu Pro Thr His
    570                 575                 580

aca cgt gcg ctc tct gtg cgc caa gct ccg ctg gct gcg gtt ggc atg      1950
Thr Arg Ala Leu Ser Val Arg Gln Ala Pro Leu Ala Ala Val Gly Met
585                 590                 595                 600

gat gga tta gag aaa cac cgt ctc gtc tcc agg act cac tct tcc cct      1998
Asp Gly Leu Glu Lys His Arg Leu Val Ser Arg Thr His Ser Ser Pro
                605                 610                 615

gct gcc tct gtt tta cct cac cca gca atg gac cgc ccc ctc cag cct      2046
Ala Ala Ser Val Leu Pro His Pro Ala Met Asp Arg Pro Leu Gln Pro
            620                 625                 630

ggc tct gca act gga att gcc tat gac ccc ttg atg ctg aaa cac cag      2094
Gly Ser Ala Thr Gly Ile Ala Tyr Asp Pro Leu Met Leu Lys His Gln
        635                 640                 645

tgc gtt tgt ggc aat tcc acc acc cac cct gag cat gct gga cga ata      2142
Cys Val Cys Gly Asn Ser Thr Thr His Pro Glu His Ala Gly Arg Ile
    650                 655                 660

cag agt atc tgg tca cga ctg caa gaa act ggg ctg cta aat aaa tgt      2190
Gln Ser Ile Trp Ser Arg Leu Gln Glu Thr Gly Leu Leu Asn Lys Cys
665                 670                 675                 680

gag cga att caa ggt cga aaa gcc agc ctg gag gaa ata cag ctt gtt      2238
Glu Arg Ile Gln Gly Arg Lys Ala Ser Leu Glu Glu Ile Gln Leu Val
                685                 690                 695

cat tct gaa cat cac tca ctg ttg tat ggc acc aac ccc ctg gac gga      2286
His Ser Glu His His Ser Leu Leu Tyr Gly Thr Asn Pro Leu Asp Gly
            700                 705                 710

cag aag ctg gac ccc agg ata ctc cta ggt gat gac tct caa aag ttt      2334
Gln Lys Leu Asp Pro Arg Ile Leu Leu Gly Asp Asp Ser Gln Lys Phe
        715                 720                 725

ttt tcc tca tta cct tgt ggt gga ctt ggg gtg gac agt gac acc att      2382
Phe Ser Ser Leu Pro Cys Gly Gly Leu Gly Val Asp Ser Asp Thr Ile
    730                 735                 740

tgg aat gag cta cgc tcg tcc ggt gct gca cgc atg gct gtt ggc tgt      2430
Trp Asn Glu Leu Arg Ser Ser Gly Ala Ala Arg Met Ala Val Gly Cys
745                 750                 755                 760

gtc atc gag ctg gct tcc aaa gtg gcc tca gga gag ctg aag aat ggg      2478
Val Ile Glu Leu Ala Ser Lys Val Ala Ser Gly Glu Leu Lys Asn Gly
                765                 770                 775

ttt gct gtt gtg agg ccc cct ggc cat cac gct gaa gaa tcc aca gcc      2526
Phe Ala Val Val Arg Pro Pro Gly His His Ala Glu Glu Ser Thr Ala
            780                 785                 790
```

-continued

```
atg ggg ttc tgc ttt ttt aat tca gtt gca att acc gcc aaa tac ttg     2574
Met Gly Phe Cys Phe Phe Asn Ser Val Ala Ile Thr Ala Lys Tyr Leu
        795                 800                 805

aga gac caa cta aat ata agc aag ata ttg att gta gat ctg gat gtt     2622
Arg Asp Gln Leu Asn Ile Ser Lys Ile Leu Ile Val Asp Leu Asp Val
    810                 815                 820

cac cat gga aac ggt acc cag cag gcc ttt tat gct gac ccc agc atc     2670
His His Gly Asn Gly Thr Gln Gln Ala Phe Tyr Ala Asp Pro Ser Ile
825                 830                 835                 840

ctg tac att tca ctc cat cgc tat gat gaa ggg aac ttt ttc cct ggc     2718
Leu Tyr Ile Ser Leu His Arg Tyr Asp Glu Gly Asn Phe Phe Pro Gly
                845                 850                 855

agt gga gcc cca aat gag gtt gga aca ggc ctt gga gaa ggg tac aat     2766
Ser Gly Ala Pro Asn Glu Val Gly Thr Gly Leu Gly Glu Gly Tyr Asn
            860                 865                 870

ata aat att gcc tgg aca ggt ggc ctt gat cct ccc atg gga gat gtt     2814
Ile Asn Ile Ala Trp Thr Gly Gly Leu Asp Pro Pro Met Gly Asp Val
        875                 880                 885

gag tac ctt gaa gca ttc agg acc atc gtg aag cct gtg gcc aaa gag     2862
Glu Tyr Leu Glu Ala Phe Arg Thr Ile Val Lys Pro Val Ala Lys Glu
    890                 895                 900

ttt gat cca gac atg gtc tta gta tct gct gga ttt gat gca ttg gaa     2910
Phe Asp Pro Asp Met Val Leu Val Ser Ala Gly Phe Asp Ala Leu Glu
905                 910                 915                 920

ggc cac acc cct cct cta gga ggg tac aaa gtg acg gca aaa tgt ttt     2958
Gly His Thr Pro Pro Leu Gly Gly Tyr Lys Val Thr Ala Lys Cys Phe
                925                 930                 935

ggt cat ttg acg aag caa ttg atg aca ttg gct gat gga cgt gtg gtg     3006
Gly His Leu Thr Lys Gln Leu Met Thr Leu Ala Asp Gly Arg Val Val
            940                 945                 950

ttg gct cta gaa gga gga cat gat ctc aca gcc atc tgt gat gca tca     3054
Leu Ala Leu Glu Gly Gly His Asp Leu Thr Ala Ile Cys Asp Ala Ser
        955                 960                 965

gaa gcc tgt gta aat gcc ctt cta gga aat gag ctg gag cca ctt gca     3102
Glu Ala Cys Val Asn Ala Leu Leu Gly Asn Glu Leu Glu Pro Leu Ala
    970                 975                 980

gaa gat att ctc cac caa agc ccg aat atg aat gct gtt att tct tta     3150
Glu Asp Ile Leu His Gln Ser Pro Asn Met Asn Ala Val Ile Ser Leu
985                 990                 995                 1000

cag aag atc att gaa att caa agc aag tat tgg aag tca gta agg atg     3198
Gln Lys Ile Ile Glu Ile Gln Ser Lys Tyr Trp Lys Ser Val Arg Met
                1005                1010                1015

gtg gct gtg cca agg ggc tgt gct ctg gct ggt gct cag ttg caa gag     3246
Val Ala Val Pro Arg Gly Cys Ala Leu Ala Gly Ala Gln Leu Gln Glu
            1020                1025                1030

gag aca gag acc gtt tct gcc ctg gcc tcc cta aca gtg gat gtg gaa     3294
Glu Thr Glu Thr Val Ser Ala Leu Ala Ser Leu Thr Val Asp Val Glu
        1035                1040                1045

cag ccc ttt gct cag gaa gac agc aga act gct ggt gag cct atg gaa     3342
Gln Pro Phe Ala Gln Glu Asp Ser Arg Thr Ala Gly Glu Pro Met Glu
    1050                1055                1060

gag gag cca gcc ttg tga agtgccaagt ccccctctga tatttcctgt            3390
Glu Glu Pro Ala Leu
1065

gtgtgacatc attgtgtatc cccccacccc agtaccctca gacatgtctt gtctgctgcc   3450

tgggtggcac agattcaatg gaacataaac actgggcaca aaattctgaa cagcagcttc   3510

acttgttctt tggatggact tgaaagggca ttaaagattc cttaaacgta accgctgtga   3570
```

-continued

```
ttctagagtt acagtaaacc acgattggaa gaaactgctt ccagcatgct tttaatatgc   3630

tgggtgaccc actcctagac accaagtttg aactagaaac attcagtaca gcactagata   3690

ttgttaattt cagaagctat gacagccagt gaaattttgg gcaaaacctg agacatagtc   3750

attcctgaca ttctgatcag cttttttttgg ggtaatttgt ttttcaaaca gtcttaactt   3810

gtttacaaga tttgctttta gctatgaacg gatcgtaatt ccacccagaa tgtaatgttt   3870

cttgtttgtt tgttttgttt tgttagggtt tttttctcaa ctttaacaca cagttcaact   3930

gttcctagta aaagttcaag atgga                                         3955


<210> SEQ ID NO 2
<211> LENGTH: 1069
<212> TYPE: PRT
<213> ORGANISM: Homo sapiens

<400> SEQUENCE: 2

Met His Ser Met Ile Ser Ser Val Asp Val Lys Ser Glu Val Pro Val
  1               5                  10                  15

Gly Leu Glu Pro Ile Ser Pro Leu Asp Leu Arg Thr Asp Leu Arg Met
             20                  25                  30

Met Met Pro Val Val Asp Pro Val Val Arg Glu Lys Gln Leu Gln Gln
         35                  40                  45

Glu Leu Leu Leu Ile Gln Gln Gln Gln Gln Ile Gln Lys Gln Leu Leu
     50                  55                  60

Ile Ala Glu Phe Gln Lys Gln His Glu Asn Leu Thr Arg Gln His Gln
 65                  70                  75                  80

Ala Gln Leu Gln Glu His Ile Lys Leu Gln Gln Glu Leu Leu Ala Ile
                 85                  90                  95

Lys Gln Gln Gln Glu Leu Leu Glu Lys Glu Gln Lys Leu Glu Gln Gln
            100                 105                 110

Arg Gln Glu Gln Glu Val Glu Arg His Arg Arg Glu Gln Gln Leu Pro
        115                 120                 125

Pro Leu Arg Gly Lys Asp Arg Gly Arg Glu Arg Ala Val Ala Ser Thr
    130                 135                 140

Glu Val Lys Gln Lys Leu Gln Glu Phe Leu Leu Ser Lys Ser Ala Thr
145                 150                 155                 160

Lys Asp Thr Pro Thr Asn Gly Lys Asn His Ser Val Ser Arg His Pro
                165                 170                 175

Lys Leu Trp Tyr Thr Ala Ala His His Thr Ser Leu Asp Gln Ser Ser
            180                 185                 190

Pro Pro Leu Ser Gly Thr Ser Pro Ser Tyr Lys Tyr Thr Leu Pro Gly
        195                 200                 205

Ala Gln Asp Ala Lys Asp Asp Phe Pro Leu Arg Lys Thr Ala Ser Glu
    210                 215                 220

Pro Asn Leu Lys Val Arg Ser Arg Leu Lys Gln Lys Val Ala Glu Arg
225                 230                 235                 240

Arg Ser Ser Pro Leu Leu Arg Arg Lys Asp Gly Asn Val Val Thr Ser
                245                 250                 255

Phe Lys Lys Arg Met Phe Glu Val Thr Glu Ser Ser Val Ser Ser Ser
            260                 265                 270

Ser Pro Gly Ser Gly Pro Ser Ser Pro Asn Asn Gly Pro Thr Gly Ser
        275                 280                 285

Val Thr Glu Asn Glu Thr Ser Val Leu Pro Pro Thr Pro His Ala Glu
    290                 295                 300
```

-continued

```
Gln Met Val Ser Gln Gln Arg Ile Leu Ile His Glu Asp Ser Met Asn
305                 310                 315                 320

Leu Leu Ser Leu Tyr Thr Ser Pro Ser Leu Pro Asn Ile Thr Leu Gly
                325                 330                 335

Leu Pro Ala Val Pro Ser Gln Leu Asn Ala Ser Asn Ser Leu Lys Glu
            340                 345                 350

Lys Gln Lys Cys Glu Thr Gln Thr Leu Arg Gln Gly Val Pro Leu Pro
        355                 360                 365

Gly Gln Tyr Gly Gly Ser Ile Pro Ala Ser Ser Ser His Pro His Val
    370                 375                 380

Thr Leu Glu Gly Lys Pro Pro Asn Ser Ser His Gln Ala Leu Leu Gln
385                 390                 395                 400

His Leu Leu Leu Lys Glu Gln Met Arg Gln Gln Lys Leu Leu Val Ala
                405                 410                 415

Gly Gly Val Pro Leu His Pro Gln Ser Pro Leu Ala Thr Lys Glu Arg
            420                 425                 430

Ile Ser Pro Gly Ile Arg Gly Thr His Lys Leu Pro Arg His Arg Pro
        435                 440                 445

Leu Asn Arg Thr Gln Ser Ala Pro Leu Pro Gln Ser Thr Leu Ala Gln
    450                 455                 460

Leu Val Ile Gln Gln Gln His Gln Gln Phe Leu Glu Lys Gln Lys Gln
465                 470                 475                 480

Tyr Gln Gln Gln Ile His Met Asn Lys Leu Leu Ser Lys Ser Ile Glu
                485                 490                 495

Gln Leu Lys Gln Pro Gly Ser His Leu Glu Glu Ala Glu Glu Glu Leu
            500                 505                 510

Gln Gly Asp Gln Ala Met Gln Glu Asp Arg Ala Pro Ser Ser Gly Asn
        515                 520                 525

Ser Thr Arg Ser Asp Ser Ser Ala Cys Val Asp Asp Thr Leu Gly Gln
    530                 535                 540

Val Gly Ala Val Lys Val Lys Glu Glu Pro Val Asp Ser Asp Glu Asp
545                 550                 555                 560

Ala Gln Ile Gln Glu Met Glu Ser Gly Glu Gln Ala Ala Phe Met Gln
                565                 570                 575

Gln Pro Phe Leu Glu Pro Thr His Thr Arg Ala Leu Ser Val Arg Gln
            580                 585                 590

Ala Pro Leu Ala Ala Val Gly Met Asp Gly Leu Glu Lys His Arg Leu
        595                 600                 605

Val Ser Arg Thr His Ser Ser Pro Ala Ala Ser Val Leu Pro His Pro
    610                 615                 620

Ala Met Asp Arg Pro Leu Gln Pro Gly Ser Ala Thr Gly Ile Ala Tyr
625                 630                 635                 640

Asp Pro Leu Met Leu Lys His Gln Cys Val Cys Gly Asn Ser Thr Thr
                645                 650                 655

His Pro Glu His Ala Gly Arg Ile Gln Ser Ile Trp Ser Arg Leu Gln
            660                 665                 670

Glu Thr Gly Leu Leu Asn Lys Cys Glu Arg Ile Gln Gly Arg Lys Ala
        675                 680                 685

Ser Leu Glu Glu Ile Gln Leu Val His Ser Glu His His Ser Leu Leu
    690                 695                 700

Tyr Gly Thr Asn Pro Leu Asp Gly Gln Lys Leu Asp Pro Arg Ile Leu
705                 710                 715                 720

Leu Gly Asp Asp Ser Gln Lys Phe Phe Ser Ser Leu Pro Cys Gly Gly
```

-continued

```
                725                 730                 735

Leu Gly Val Asp Ser Asp Thr Ile Trp Asn Glu Leu Arg Ser Ser Gly
            740                 745                 750

Ala Ala Arg Met Ala Val Gly Cys Val Ile Glu Leu Ala Ser Lys Val
        755                 760                 765

Ala Ser Gly Glu Leu Lys Asn Gly Phe Ala Val Val Arg Pro Pro Gly
    770                 775                 780

His His Ala Glu Glu Ser Thr Ala Met Gly Phe Cys Phe Phe Asn Ser
785                 790                 795                 800

Val Ala Ile Thr Ala Lys Tyr Leu Arg Asp Gln Leu Asn Ile Ser Lys
                805                 810                 815

Ile Leu Ile Val Asp Leu Asp Val His His Gly Asn Gly Thr Gln Gln
            820                 825                 830

Ala Phe Tyr Ala Asp Pro Ser Ile Leu Tyr Ile Ser Leu His Arg Tyr
        835                 840                 845

Asp Glu Gly Asn Phe Phe Pro Gly Ser Gly Ala Pro Asn Glu Val Gly
    850                 855                 860

Thr Gly Leu Gly Glu Gly Tyr Asn Ile Asn Ile Ala Trp Thr Gly Gly
865                 870                 875                 880

Leu Asp Pro Pro Met Gly Asp Val Glu Tyr Leu Glu Ala Phe Arg Thr
                885                 890                 895

Ile Val Lys Pro Val Ala Lys Glu Phe Asp Pro Asp Met Val Leu Val
            900                 905                 910

Ser Ala Gly Phe Asp Ala Leu Glu Gly His Thr Pro Pro Leu Gly Gly
        915                 920                 925

Tyr Lys Val Thr Ala Lys Cys Phe Gly His Leu Thr Lys Gln Leu Met
    930                 935                 940

Thr Leu Ala Asp Gly Arg Val Val Leu Ala Leu Glu Gly Gly His Asp
945                 950                 955                 960

Leu Thr Ala Ile Cys Asp Ala Ser Glu Ala Cys Val Asn Ala Leu Leu
                965                 970                 975

Gly Asn Glu Leu Glu Pro Leu Ala Glu Asp Ile Leu His Gln Ser Pro
            980                 985                 990

Asn Met Asn Ala Val Ile Ser Leu Gln Lys Ile Ile Glu Ile Gln Ser
        995                 1000                1005

Lys Tyr Trp Lys Ser Val Arg Met Val Ala Val Pro Arg Gly Cys Ala
    1010                1015                1020

Leu Ala Gly Ala Gln Leu Gln Glu Glu Thr Glu Thr Val Ser Ala Leu
1025                1030                1035                1040

Ala Ser Leu Thr Val Asp Val Glu Gln Pro Phe Ala Gln Glu Asp Ser
                1045                1050                1055

Arg Thr Ala Gly Glu Pro Met Glu Glu Glu Pro Ala Leu
            1060                1065


<210> SEQ ID NO 3
<211> LENGTH: 51
<212> TYPE: DNA
<213> ORGANISM: Homo sapiens
<220> FEATURE:
<221> NAME/KEY: CDS
<222> LOCATION: (1)..(51)

<400> SEQUENCE: 3

gta ata ggc aaa gat tta gct cca gga ttt gta att aaa gtc att atc       48
Val Ile Gly Lys Asp Leu Ala Pro Gly Phe Val Ile Lys Val Ile Ile
  1               5                  10                  15
```

-continued tga 51

<210> SEQ ID NO 4
<211> LENGTH: 16
<212> TYPE: PRT
<213> ORGANISM: Homo sapiens

<400> SEQUENCE: 4

Val Ile Gly Lys Asp Leu Ala Pro Gly Phe Val Ile Lys Val Ile Ile
1 5 10 15

<210> SEQ ID NO 5
<211> LENGTH: 1042
<212> TYPE: DNA
<213> ORGANISM: Homo sapiens

<400> SEQUENCE: 5
ggccttggag aagggtacaa tataaatatt gcctggacag gtggccttga tcctcccatg 60
ggagatgttg agtaccttga agcattcagg accatcgtga agcctgtggc caaagagttt 120
gatccagaca tggtcttagt atctgctgga tttgatgcat tggaaggcca cacccctcct 180
ctaggagggt acaaagtgac ggcaaaatgt tttggtcatt tgacgaagca attgatgaca 240
ttggctgatg gacgtgtggt gttggctcta gaaggaggac atgatctcac agccatctgt 300
gatgcatcag aagcctgtgt aaatgccctt ctaggaaatg agctggagcc acttgcagaa 360
gatattctcc accaaagccc gaatatgaat gctgttattt ctttacagaa gatcattgaa 420
attcaaagca agtattggaa gtcagtaagg atggtggctg tgccaagggg ctgtgctctg 480
gctggtgctc agttgcaaga ggagacagag accgtttctg ccctggcctc cctaacagtg 540
gatgtggaac agccctttgc tcaggaagac agcagaactg ctggtgagcc tatggaagag 600
gagccagcct tgtgaagtgc caagtccccc tctgatattt cctgtgtgtg acatcattgt 660
gtatcccccc accccagtac cctcagacat gtcttgtctg ctgcctgggt ggcacagatt 720
caatggaaca taaacactgg gcacaaaatt ctgaacagca gcttcacttg ttctttggat 780
ggacttgaaa gggcattaaa gattccttaa acgtaaccgc tgtgattcta gagttacagt 840
aaaccacgat tggaagaaac tgcttccagc atgcttttaa tatgctgggt gacccactcc 900
tagacaccaa gtttgaacta gaaacattca gtacagcact agatattgtt aatttcagaa 960
gctatgacag ccagtgaaat tttgggcaaa acctgagaca tagtcattcc tgacattctg 1020
atcagctttt tttggggtaa tt 1042

<210> SEQ ID NO 6
<211> LENGTH: 207
<212> TYPE: DNA
<213> ORGANISM: Homo sapiens

<400> SEQUENCE: 6
ggccttggag aagggtacaa tataaatatt gcctggacag gtggccttga tcctcccatg 60
ggagatgttg agtaccttga agcattcagg accatcgtga agcctgtggc aaagagtttg 120
atccagacat ggtcttagta tctgctggat ttgatgcatt ggaaggccac acccctcctc 180
taggagggta caaagtgacg gcaaaat 207

<210> SEQ ID NO 7
<211> LENGTH: 276
<212> TYPE: DNA
<213> ORGANISM: Homo sapiens -continued

<400> SEQUENCE: 7

```
gatgcattgg aaggccacac ccctcctcta gggtttttcg aaagtgacgg caaaatgttt     60
tggtcatttg acgaagcaat tgatgacatt ggctgatgga cgtgtggtgt tggctctaga    120
aggaggacat gatctcacag ccatctgtga tgcatcagaa gcctgtgtaa atgcccttct    180
aggaaatgag ctggagccac ttgcagaaga tattctcctc caaagcccga atatgaatgc    240
tgttatttct ttacagaaga tcattgaaat tcaaag                              276
```

<210> SEQ ID NO 8
<211> LENGTH: 355
<212> TYPE: DNA
<213> ORGANISM: Homo sapiens
<220> FEATURE:
<221> NAME/KEY: misc_feature
<222> LOCATION: (63, 121, 160, 215, 235, 279, 329, 349)
<223> OTHER INFORMATION: n is a or g or c or t

<400> SEQUENCE: 8

```
tctttacaga agatcattga aattcaaagc aagtattgga agtcagtaag gatggtggct     60
gtnccaaggg gctgtcctct ggctggtgct cagttgcaag aggagacaga gaccgtttct    120
nccctggcct ccctaacagt ggatgtggaa cagccctttn ctcaggaaga cagcagaact    180
gctggtgagc ctatggaaga ggagccagcc ttgtnaagtg ccaagtcccc ctctnatatt    240
tcctgtgtgt gacatcattg tgtatccccc caccccagna ccctcagaca tgatctttgt    300
ctgctgactg ggtggcacag aattcaatng aacataaaca actgggcana aaatt         355
```

<210> SEQ ID NO 9
<211> LENGTH: 392
<212> TYPE: DNA
<213> ORGANISM: Homo sapiens

<400> SEQUENCE: 9

```
acatcattgg gtatcccccc accccagtac cctcagacat gtcttgtctg ctgcctgggt     60
ggcacagatt caatggaaca tgaacactgg gcacaaaatt ctgaacagca gcttcacttg    120
ttctttggat ggacttgaaa gggcattaaa gattccttaa acgtaaccgc tgtgattcta    180
gagttacagt aaaccacgat tggaggaaac tgcttccagc atgcttttaa tatgctgggt    240
gacccactcc tagacaccaa gtttgaacta gaaacattca gtacagcact agatattgtt    300
aatttcagaa gctatgacag ccagtgaaat tttgggcaaa acctgagaca tagtcattcc    360
tgacattctg atcagctttt tttggggtaa tt                                  392
```

<210> SEQ ID NO 10
<211> LENGTH: 22
<212> TYPE: DNA
<213> ORGANISM: Homo sapiens

<400> SEQUENCE: 10

```
tctaagccag gtttaattgg tt                                              22
```

<210> SEQ ID NO 11
<211> LENGTH: 22
<212> TYPE: DNA
<213> ORGANISM: Homo sapiens

<400> SEQUENCE: 11

```
gtttttcctc agatggggtg gc                                              22
```

-continued

<210> SEQ ID NO 12
<211> LENGTH: 22
<212> TYPE: DNA
<213> ORGANISM: Homo sapiens

<400> SEQUENCE: 12
atcagctcag gtaagatcct ct 22

<210> SEQ ID NO 13
<211> LENGTH: 22
<212> TYPE: DNA
<213> ORGANISM: Homo sapiens

<400> SEQUENCE: 13
ctggttcttt agtggatgtg aa 22

<210> SEQ ID NO 14
<211> LENGTH: 22
<212> TYPE: DNA
<213> ORGANISM: Homo sapiens

<400> SEQUENCE: 14
gcatatcaag gtagcaaatg ct 22

<210> SEQ ID NO 15
<211> LENGTH: 22
<212> TYPE: DNA
<213> ORGANISM: Homo sapiens

<400> SEQUENCE: 15
tcttctcgca agttgcaaca gg 22

<210> SEQ ID NO 16
<211> LENGTH: 22
<212> TYPE: DNA
<213> ORGANISM: Homo sapiens

<400> SEQUENCE: 16
aagttgcaac aggaacttct ag 22

<210> SEQ ID NO 17
<211> LENGTH: 22
<212> TYPE: DNA
<213> ORGANISM: Homo sapiens

<400> SEQUENCE: 17
ggacgagaaa gtaagaggca cc 22

<210> SEQ ID NO 18
<211> LENGTH: 22
<212> TYPE: DNA
<213> ORGANISM: Homo sapiens

<400> SEQUENCE: 18
aggcaccagg gtaaacgatg ga 22

<210> SEQ ID NO 19
<211> LENGTH: 22
<212> TYPE: DNA
<213> ORGANISM: Homo sapiens

<400> SEQUENCE: 19
tgtgtatttc aggggcagtg gc 22

```
<210> SEQ ID NO 20
<211> LENGTH: 22
<212> TYPE: DNA
<213> ORGANISM: Homo sapiens

<400> SEQUENCE: 20

tctggtacac gtatgttcag tg                                            22

<210> SEQ ID NO 21
<211> LENGTH: 22
<212> TYPE: DNA
<213> ORGANISM: Homo sapiens

<400> SEQUENCE: 21

tgtcttttct agggctgccc ac                                            22

<210> SEQ ID NO 22
<211> LENGTH: 22
<212> TYPE: DNA
<213> ORGANISM: Homo sapiens

<400> SEQUENCE: 22

cgaaaaactg gtaagttggt tt                                            22

<210> SEQ ID NO 23
<211> LENGTH: 22
<212> TYPE: DNA
<213> ORGANISM: Homo sapiens

<400> SEQUENCE: 23

ctcaatcccc agcctctgag cc                                            22

<210> SEQ ID NO 24
<211> LENGTH: 22
<212> TYPE: DNA
<213> ORGANISM: Homo sapiens

<400> SEQUENCE: 24

gaggtgacag gtaattgagg ac                                            22

<210> SEQ ID NO 25
<211> LENGTH: 22
<212> TYPE: DNA
<213> ORGANISM: Homo sapiens

<400> SEQUENCE: 25

aatatttttc agaatcctca gt                                            22

<210> SEQ ID NO 26
<211> LENGTH: 22
<212> TYPE: DNA
<213> ORGANISM: Homo sapiens

<400> SEQUENCE: 26

tcatgccgag gtaagaccct ta                                            22

<210> SEQ ID NO 27
<211> LENGTH: 22
<212> TYPE: DNA
<213> ORGANISM: Homo sapiens

<400> SEQUENCE: 27
```

-continued ttttttttaac agcaaatggt tt 22

<210> SEQ ID NO 28
<211> LENGTH: 22
<212> TYPE: DNA
<213> ORGANISM: Homo sapiens

<400> SEQUENCE: 28
ccagctcaat gtaagtcatt gc 22

<210> SEQ ID NO 29
<211> LENGTH: 22
<212> TYPE: DNA
<213> ORGANISM: Homo sapiens

<400> SEQUENCE: 29
ttctcaacac aggcttcgaa tt 22

<210> SEQ ID NO 30
<211> LENGTH: 22
<212> TYPE: DNA
<213> ORGANISM: Homo sapiens

<400> SEQUENCE: 30
cttgtagctg gtaattcatt at 22

<210> SEQ ID NO 31
<211> LENGTH: 22
<212> TYPE: DNA
<213> ORGANISM: Homo sapiens

<400> SEQUENCE: 31 ttttttttttc aggtggagtt cc 22

<210> SEQ ID NO 32
<211> LENGTH: 22
<212> TYPE: DNA
<213> ORGANISM: Homo sapiens

<400> SEQUENCE: 32
catgaacaaa gtaagcctcc aa 22

<210> SEQ ID NO 33
<211> LENGTH: 22
<212> TYPE: DNA
<213> ORGANISM: Homo sapiens

<400> SEQUENCE: 33
actctcttct agctgctttc ga 22

<210> SEQ ID NO 34
<211> LENGTH: 22
<212> TYPE: DNA
<213> ORGANISM: Homo sapiens

<400> SEQUENCE: 34
tatgcaacag gtaataggca aa 22

<210> SEQ ID NO 35
<211> LENGTH: 22
<212> TYPE: DNA
<213> ORGANISM: Homo sapiens

<400> SEQUENCE: 35

-continued tcttggcaac agcctttcct gg 22

<210> SEQ ID NO 36
<211> LENGTH: 22
<212> TYPE: DNA
<213> ORGANISM: Homo sapiens

<400> SEQUENCE: 36
tctgcaactg gtaggaatcc ct 22

<210> SEQ ID NO 37
<211> LENGTH: 22
<212> TYPE: DNA
<213> ORGANISM: Homo sapiens

<400> SEQUENCE: 37
cttgtcttaa aggaattgcc ta 22

<210> SEQ ID NO 38
<211> LENGTH: 22
<212> TYPE: DNA
<213> ORGANISM: Homo sapiens

<400> SEQUENCE: 38
taaatgtgag gtaatccaga at 22

<210> SEQ ID NO 39
<211> LENGTH: 22
<212> TYPE: DNA
<213> ORGANISM: Homo sapiens

<400> SEQUENCE: 39
attttcttgc agcgaattca ag 22

<210> SEQ ID NO 40
<211> LENGTH: 22
<212> TYPE: DNA
<213> ORGANISM: Homo sapiens

<400> SEQUENCE: 40
atactcctag gtctgtacgg gc 22

<210> SEQ ID NO 41
<211> LENGTH: 22
<212> TYPE: DNA
<213> ORGANISM: Homo sapiens

<400> SEQUENCE: 41
cttactgtat aggtgatgac tc 22

<210> SEQ ID NO 42
<211> LENGTH: 22
<212> TYPE: DNA
<213> ORGANISM: Homo sapiens

<400> SEQUENCE: 42
tggacttggg gtaagtacaa gt 22

<210> SEQ ID NO 43
<211> LENGTH: 22
<212> TYPE: DNA
<213> ORGANISM: Homo sapiens -continued

<400> SEQUENCE: 43
ctgtttgctc aggtggacag tg 22

<210> SEQ ID NO 44
<211> LENGTH: 22
<212> TYPE: DNA
<213> ORGANISM: Homo sapiens

<400> SEQUENCE: 44
agagctgaag gtgaggtccg gg 22

<210> SEQ ID NO 45
<211> LENGTH: 22
<212> TYPE: DNA
<213> ORGANISM: Homo sapiens

<400> SEQUENCE: 45
ttgttttcac agaatgggtt tg 22

<210> SEQ ID NO 46
<211> LENGTH: 22
<212> TYPE: DNA
<213> ORGANISM: Homo sapiens

<400> SEQUENCE: 46
ccacagccat gtaagtacca gg 22

<210> SEQ ID NO 47
<211> LENGTH: 22
<212> TYPE: DNA
<213> ORGANISM: Homo sapiens

<400> SEQUENCE: 47
tctattccgc aggggggttct gc 22

<210> SEQ ID NO 48
<211> LENGTH: 22
<212> TYPE: DNA
<213> ORGANISM: Homo sapiens

<400> SEQUENCE: 48
tgtagatctg gtatgtattc ct 22

<210> SEQ ID NO 49
<211> LENGTH: 22
<212> TYPE: DNA
<213> ORGANISM: Homo sapiens

<400> SEQUENCE: 49
atttccctgt aggatgttca cc 22

<210> SEQ ID NO 50
<211> LENGTH: 22
<212> TYPE: DNA
<213> ORGANISM: Homo sapiens

<400> SEQUENCE: 50
cccaaatgag gttcggttta tt 22

<210> SEQ ID NO 51
<211> LENGTH: 22
<212> TYPE: DNA
<213> ORGANISM: Homo sapiens -continued

<400> SEQUENCE: 51
ttctcttccc aggttggaac ag 22

<210> SEQ ID NO 52
<211> LENGTH: 22
<212> TYPE: DNA
<213> ORGANISM: Homo sapiens

<400> SEQUENCE: 52
aagcattcag gttggtactt ct 22

<210> SEQ ID NO 53
<211> LENGTH: 22
<212> TYPE: DNA
<213> ORGANISM: Homo sapiens

<400> SEQUENCE: 53
tttactgtgc aggaccatcg tg 22

<210> SEQ ID NO 54
<211> LENGTH: 22
<212> TYPE: DNA
<213> ORGANISM: Homo sapiens

<400> SEQUENCE: 54
acggcaaaat gtaagtacct ct 22

<210> SEQ ID NO 55
<211> LENGTH: 22
<212> TYPE: DNA
<213> ORGANISM: Homo sapiens

<400> SEQUENCE: 55
gtattatggt aggttttggt ca 22

<210> SEQ ID NO 56
<211> LENGTH: 22
<212> TYPE: DNA
<213> ORGANISM: Homo sapiens

<400> SEQUENCE: 56
aggaaatgag gtaaaaaagt aa 22

<210> SEQ ID NO 57
<211> LENGTH: 22
<212> TYPE: DNA
<213> ORGANISM: Homo sapiens

<400> SEQUENCE: 57
ctattcttgc agctggagcc ac 22

<210> SEQ ID NO 58
<211> LENGTH: 22
<212> TYPE: DNA
<213> ORGANISM: Homo sapiens

<400> SEQUENCE: 58
gaaattcaaa gtatgtcttt aa 22

<210> SEQ ID NO 59
<211> LENGTH: 22
<212> TYPE: DNA

-continued

<213> ORGANISM: Homo sapiens

<400> SEQUENCE: 59
tgtttttcct aggcaagtat tg 22

<210> SEQ ID NO 60
<211> LENGTH: 22
<212> TYPE: DNA
<213> ORGANISM: Homo sapiens

<400> SEQUENCE: 60
aagacagcag gtatgaatcc aa 22

<210> SEQ ID NO 61
<211> LENGTH: 22
<212> TYPE: DNA
<213> ORGANISM: Homo sapiens

<400> SEQUENCE: 61
ttatttttac agaactgctg gt 22

<210> SEQ ID NO 62
<211> LENGTH: 240
<212> TYPE: DNA
<213> ORGANISM: Homo sapiens

<400> SEQUENCE: 62
cacactctca tgtctttctc ttctcgcaag ttgcaacagg aacttctagc cataaaacag 60
caacaagaac tcctagaaaa ggagcagaaa ctggagcagc agaggcaaga acaggaagta 120
gagaggcatc gcagagaaca gcagcttcct cctctcagag gcaaagatag aggacgagaa 180
agtaagaggc accagggtaa acgatggact ctctttcctc atcgttagct gatcattatt 240

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 63
atgcacagta tgatcagctc a 21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 64
gtcacacaca ggaaatatca g 21

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 65
tcagataatg actttaatta caaat 25

-continued

```
<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 66

tctctaatcc atccatgcca a                                       21


<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 67

aggctgcttt tatgcaacag                                         20


<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 68

ctgaatgctt caaggtactc a                                       21
```